United States Patent
Andrés-Gil et al.

(10) Patent No.: US 7,265,103 B2
(45) Date of Patent: Sep. 4, 2007

(54) SUBSTITUTED AMINO ISOXAZOLINE DERIVATIVES AND THEIR USE AS ANTI-DEPRESSANTS

(75) Inventors: José Ignacio Andrés-Gil, Madrid (ES); Manuel Jesús Alcázar-Vaca, Toledo (ES); Margaretha Henrica Maria Bakker, Alsbach-Haehnlein (DE); Ana Isabel De Lucas Olivares, Toledo (ES)

(73) Assignee: Janssen Pharmaceutica NV., Beerse (BE)

( * ) Notice: Subject to any disclaimer, the term of this patent is extended or adjusted under 35 U.S.C. 154(b) by 0 days.

(21) Appl. No.: 10/510,220

(22) PCT Filed: Mar. 27, 2003

(86) PCT No.: PCT/EP03/03245

§ 371 (c)(1),
(2), (4) Date: Oct. 1, 2004

(87) PCT Pub. No.: WO03/082878

PCT Pub. Date: Oct. 9, 2003

(65) Prior Publication Data

US 2005/0222125 A1 Oct. 6, 2005

(30) Foreign Application Priority Data

Apr. 2, 2002 (EP) .................. 02076239

(51) Int. Cl.
- A61K 31/55 (2006.01)
- A61K 31/5377 (2006.01)
- A61K 31/496 (2006.01)
- C07D 498/04 (2006.01)

(52) U.S. Cl. .............. 514/217.1; 514/229.5; 514/232.5; 514/253.03; 514/254.04; 514/293; 514/321; 540/599; 540/603; 544/99; 544/137; 544/361; 544/368; 546/83; 546/198

(58) Field of Classification Search ......... 544/361, 544/368, 99; 546/83, 198; 514/253.03, 514/254.04, 293, 321, 229.5
See application file for complete search history.

(56) References Cited

U.S. PATENT DOCUMENTS

2005/0256119 A1* 11/2005 Andres-Gil et al. ...... 514/234.2
2006/0122167 A1* 6/2006 Andres-Gil et al. ... 514/210.21

FOREIGN PATENT DOCUMENTS

| EP | 0361577 B1 | 5/1993 |
|----|------------|--------|
| EP | 0885883 A1 | 12/1998 |
| WO | WO97/25317 A1 | 7/1997 |
| WO | WO 02066484 A1 | 8/2002 |

OTHER PUBLICATIONS

Crow et al. Expert Opin.Investig.Drugs, vol. 12(3), p. 491-499 (2003).*
O'Neil M.J., "The Merck Index, thirteenth edition," 2001, Merck & Co., Inc., pp. 741, monography 4211.
Stella, V.J. et al., "Prodrugs Do They Have Advantages in Clinical Practice?," Drugs 29, 1985, pp. 455-473.
PCT Search Report dated Jul. 31, 2003 for PCT/EP03/03245.

* cited by examiner

*Primary Examiner*—Emily Bernhardt

(57) ABSTRACT

The invention concerns substituted amino isoxazoline derivatives, more in particular tricyclic dihydrobenzopyranoisoxazoline, dihydroquinolinoisozazoline, dihydronaphthalenoisoxazoline and dihydrobenzothiopyranoisoxazoline derivatives substituted on the phenylpart of the tricyclic moiety with primary, secondary and/or tertiary amino groups, according to Formula (I)

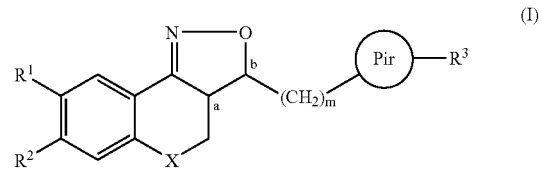

wherein $X=CH_2$, $N-R^7$, S or O, $R^1$, $R^2$ and $R^3$ are certain specific substituents, with the proviso that at least one of $R^1$ and $R^2$ is an amino radical of formula $N-R^{10}R^{11}$ wherein $R^{10}$ and $R^{11}$ are each a variety of radicals, Pir is an optionally substituted piperidyl or piperazyl radical and $R^3$ represents an optionally substituted aromatic homocyclic or heterocyclic ring system including a partially or completely hydrogenated hydrocarbon chain of maximum 6 atoms long with which the ring system is attached to the Pir radical and which may contain one or more heteroatoms selected from the group of O, N and S; a process for their preparation, pharmaceutical compositions comprising them and their use as a medicine, in particular for the treatment of depression and/of anxiety and disorders of body weight. The compounds according to the invention have surprisingly been shown to have a serotonin (5-HT) reuptake inhibitor activity in combination with additional $\alpha_2$-adrenoceptor antagonist activity and show a strong anti-depressant activity without being sedative. Compounds according to the invention are also suitable for treating depression, anxiety and body weight disorders. The invention also relates to novel combination of substituted amino isoxazoline derivatives according to the invention with antidepressants, anxiolytics and/or antipsychotics to improve efficacy and/or onset of action.

12 Claims, No Drawings

SUBSTITUTED AMINO ISOXAZOLINE DERIVATIVES AND THEIR USE AS ANTI-DEPRESSANTS

CROSS REFERENCE TO RELATED APPLICATIONS

This application is the national stage of Application No. PCT/EP03/03245, filed Mar. 27, 2003, which application claims priority from EP 02076239.9 filed Apr. 2, 2002

FIELD OF THE INVENTION

The invention concerns substituted amino isoxazoline derivatives, more in particular tricyclic dihydrobenzopyranoisoxazoline, dihydroquinolinoisozazoline, dihydronaphthalenoisoxazoline and dihydrobenzothiopyranoisoxazoline derivatives substituted on the phenylpart of the tricyclic moiety with primary, secondary and/or tertiary amino groups, processes for their preparation, pharmaceutical compositions comprising them and their use as a medicine, in particular for treating depression, anxiety, movement disorders, psychosis, schizophrenia and body weight disorders including anorexia nervosa and bulimia.

BACKGROUND OF THE INVENTION

The invention also relates to novel combination of said substituted amino isoxazolines derivatives with antidepressants, anxiolytics, antipsychotics and anti-Parkinson's disease drugs.

Tetrahydronaphthalene and indane derivatives showing anti-depressant activity are known from EP-361 577 B1. These compounds are typical monoamine reuptake blockers with additional $\alpha_2$-adrenoceptor antagonist activity and they show anti-depressant activity without being sedative.

In WO 97/25317 are disclosed tricyclic 4,5-dihydronaphth[1,2-c]isoxazole derivatives having serotonin 5-HT$_3$ antagonist activity and useful for the treatment of anxiety, psychiatric disorders, nausea, vomiting and drug dependency. They differ in chemical structure from the compounds of the present invention in the saturation of the isoxazole moiety and the substitution pattern thereof.

In EP 885 883 A1 are disclosed bicyclic fused heterocyclic compounds having dopamine D$_4$ activity and serotonin 5-HT$_2$ antagonist activity and useful as central nervous agent, in particular as antipsychotic agent. They differ in chemical structure from the compounds of the present invention in the nature of the fused heterocycle and the substitution pattern thereof.

The problems associated with the compounds according to the state of the art is that the compounds cause considerable side-effects, such as nausea, excitation, an increased heart rate and a reduced sexual function. Furthermore, it requires a long time, in particular 3-4 weeks, before the response starts.

The purpose of the present invention is to provide novel compounds derivatives for treating depression, anxiety, movement disorders, psychosis, schizophrenia and body weight disorders, in particular compounds that do not exhibit the aforementioned disadvantages.

SUMMARY OF THE INVENTION

The present invention relates to novel substituted amino isoxazoline derivatives according to the general Formula (I)

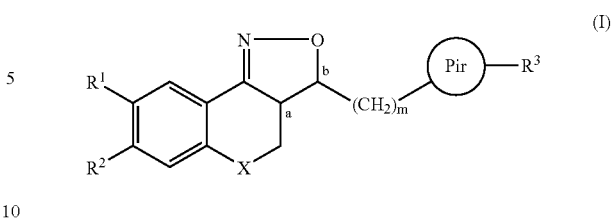

the pharmaceutically acceptable acid or base addition salts thereof, the stereochemically isomeric forms thereof and the N-oxide form thereof, wherein:

X is CH$_2$, N—R$^7$, S or O;

R$^7$ is selected from the group of hydrogen, alkyl, Ar, Ar-alkyl, alkylcarbonyl, alkyloxycarbonyl and mono- and di(alkyl)aminocarbonyl;

R$^1$ and R$^2$ are each selected from the group of hydrogen, hydroxy, cyano, halo, OSO$_2$H, OSO$_2$CH$_3$, N—R$^{10}$R$^{11}$, alkyloxy, alkyloxyalkyloxy, alkyloxyalkyloxyalkyloxy, tetrahydrofuranyloxy, alkylthio, alkylcarbonyloxy, alkyloxyalkylcarbonyloxy, pyridinylcarbonyloxy, alkylcarbonyloxyalkyloxy, alkyloxycarbonyloxy, alkenyloxy, alkenylcarbonyloxy and mono- or di(alkyl)aminoalkyloxy;

with the proviso that at least one of R$^1$ and R$^2$ is N—R$^{10}$R$^{11}$ wherein:

R$^{10}$ and R$^{11}$ are each, independently from each other, selected from the group of hydrogen, alkyl, Het, Ar, Ar-alkyl, Het-alkyl, mono- or di(alkyl)aminoalkyl, mono- or di(alkenyl)aminoalkyl, alkylcarbonyl, alkenylcarbonyl, Ar-carbonyl, Het-carbonyl, alkyloxycarbonyl, aminocarbonyl, mono- or di(alkyl)aminocarbonyl, mono- or di(Ar)aminocarbonyl, mono- or di(alkyloxycarbonylalkyl)aminocarbonyl, alkylcarbonyloxyalkyl, alkenylcarbonyloxyalkyl, mono- or di(alkyl)aminocarbonyloxyalkyl, aminoiminomethyl, alkylaminoiminomethyl, N-benzylpiperazinyliminomethyl, alkylsulphonyl and Ar-sulphonyl; or R$^{10}$ and R$^{11}$ may be taken together and with the N may form a monovalent radical selected from the group of

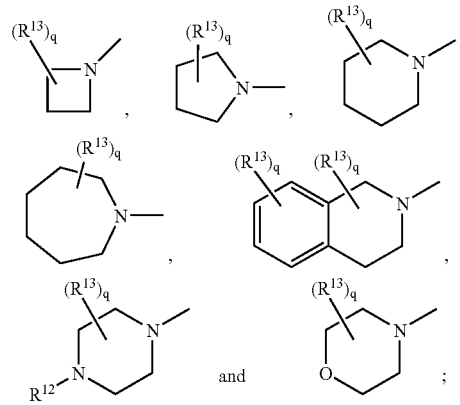

wherein:

R$^{12}$ is selected from the group of hydrogen, alkyl, Ar, Ar-alkyl, Ar-alkenyl, alkylcarbonyl, alkyloxycarbonyl, alkyloxyalkylcarbonyl and mono- or di(alkyl)aminocarbonyl;

each ring having optionally 1, 2 or 3 double bonds and each ring being optionally substituted with q radicals R[13], each radical R[13] independently from each other selected from the group of alkyl, oxo, Ar, Ar-alkyl, Ar-alkenyl and alkyloxycarbonyl and q being an integer ranging from 0 to 6; or R[1] and R[2] may be taken together to form a bivalent radical —R[1]—R[2]— selected from the group of —O—CH$_2$—NR[14]—, —NR[14]—CH$_2$—O—, —NR[15]—CH$_2$—NR[14]—, —NR[14]—CH$_2$—CH$_2$—O—, —O—CH$_2$—CH$_2$—NR[14]—, —NR[15]—CH$_2$—CH$_2$—NR[14]—, —wherein R[14] and R[15] each, independently from each other, are selected from the group of hydrogen, alkyl, Ar, Ar-alkyl, alkylcarbonyl, alkyloxycarbonyl, alkyloxyalkylcarbonyl and mono- or di(alkyl)aminocarbonyl;

a and b are asymmetric centres;

(CH$_2$)$_m$ is a straight hydrocarbon chain of m carbon atoms, m being an integer ranging from 1 to 4;

Pir is a radical according to any one of Formula (IIa), (IIb) or (IIc)

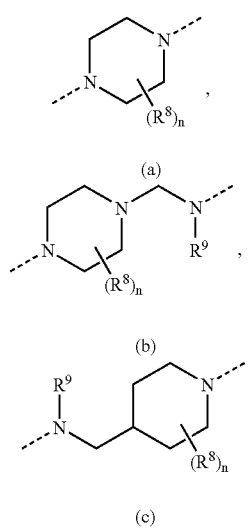

(II)

(a)

(b)

(c)

optionally substituted with n radicals R[8], wherein:

each R[8] is independently from each other, selected from the group of hydroxy, amino, nitro, cyano, halo and alkyl;

n is an integer ranging from 0 to 5;

R[9] is selected from the group of hydrogen, alkyl and formyl;

R[3] represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O, N and S;

alkyl represents a straight or branched saturated hydrocarbon radical having from 1 to 6 carbon atoms or a cyclic saturated hydrocarbon radical having from 3 to 6 carbon atoms, optionally substituted with one or more methyl, halo, cyano, oxo, hydroxy, alkyloxy or amino radicals;

alkenyl represents a straight or branched unsaturated hydrocarbon radical having one or more double bonds, optionally substituted with one or more methyl, halo, cyano, oxo, hydroxy, alkyloxy or amino radicals;

Ar represents phenyl or naphthyl, optionally substituted with one or more radicals selected from the group of alkyl, halo, cyano, oxo, hydroxy, alkyloxy and amino; and Het is a monocyclic heterocyclic radical selected from the group of azetidinyl, pyrrolidinyl, dioxolyl, imidazolidinyl, pyrrazolidinyl, piperidinyl, homopiperidinyl, dioxyl, morpholinyl, dithianyl, thiomorpholinyl, piperazinyl, imidazolidinyl, tetrahydrofuranyl, 2H-pyrrolyl, pyrrolinyl, imidazolinyl, pyrrazolinyl, pyrrolyl, imidazolyl, pyrazolyl, triazolyl, furanyl, thienyl, oxazolyl, isoxazolyl, thiazolyl, thiadiazolyl, isothiazolyl, pyridinyl, pyrimidinyl, pyrazinyl, pyridazinyl and triazinyl; each radical optionally substituted with one or more radicals selected from the group of alkyl, Ar, Ar-alkyl, halo, cyano, oxo, hydroxy, alkyloxy and amino.

DETAILED DESCRIPTION OF THE INVENTION

Preferably, the invention relates to compounds according to Formula (I), the pharmaceutically acceptable acid or base addition salts thereof, the stereochemically isomeric forms thereof and the N-oxide form thereof, wherein:

X is O;

R[1] and R[2] are each selected from the group of hydrogen, N—R[10]R[11] and alkyloxy;

with the proviso that at least one of R[1] and R[2] is N—R[10]R[11] wherein:

R[10] and R[11] are each, independently from each other, selected from the group of hydrogen, alkyl, Het, Ar, Ar-alkyl, Het-alkyl, mono- or di(alkyl)aminoalkyl, mono- or di(alkenyl)aminoalkyl, alkylcarbonyl, alkenylcarbonyl, Ar-carbonyl, Het-carbonyl, alkyloxycarbonyl, aminocarbonyl, mono- or di(alkyl)aminocarbonyl, mono- or di(Ar)aminocarbonyl, mono- or di(alkyloxycarbonylalkyl)aminocarbonyl, alkylcarbonyloxyalkyl, alkenylcarbonyloxyalkyl, mono- or di(alkyl)aminocarbonyloxyalkyl, N-benzylpiperazinyliminomethyl, alkylsulphonyl and Ar-sulphonyl; or R[10] and R[11] may be taken together and with the N may form a monovalent radical selected from the group of

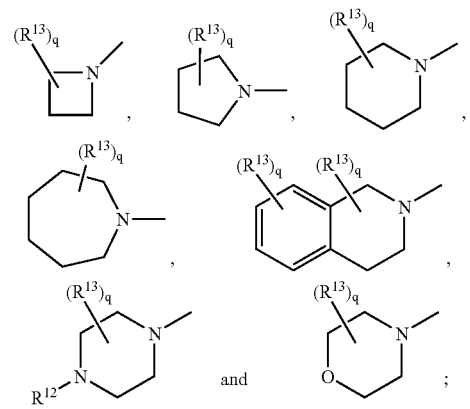

wherein:

R[12] is selected from the group of hydrogen, alkyl, Ar, Ar-alkyl and Ar-alkenyl;

each ring having optionally a double bond and each ring being optionally substituted with q radicals R[13], each radical R[13] independently from each other selected from the group of alkyl, oxo and alkyloxycarbonyl and q being an integer ranging from 0 to 2; or $R^1$ and $R^2$ may be taken together to form a bivalent radical —O—CH$_2$—CH$_2$—NR$^{14}$— wherein $R^{14}$ is selected from the group of hydrogen, alkyl, alkylcarbonyl, alkyloxyalkylcarbonyl and mono- or di(alkyl)aminocarbonyl;

a and b are asymmetric centres;

(CH$_2$)$_m$ is a straight hydrocarbon chain of m carbon atoms, m being an integer equal to 1;

Pir is a radical according to Formula (IIa)

$R^3$ represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O, N and S;

alkyl represents a straight or branched saturated hydrocarbon radical having from 1 to 6 carbon atoms or a cyclic saturated hydrocarbon radical having from 3 to 6 carbon atoms, optionally substituted with one or more methyl or amino radicals;

alkenyl represents a straight or branched unsatured hydrocarbon radical having one or more double bonds, optionally substituted with one or more methyl radicals;

Ar represents phenyl, optionally substituted with one or more radicals selected from the group of alkyl, halo, cyano, hydroxy and alkyloxy; and Het is a monocyclic heterocyclic radical selected from the group of azetidinyl, pyrrolidinyl, piperidinyl, homopiperidinyl, morpholinyl, piperazinyl, N-benzylpiperazinyl, tetrahydrofuranyl and pyridinyl.

More in particular, the invention relates to compounds according to Formula (I), the pharmaceutically acceptable acid or base addition salts thereof, the stereochemically isomeric forms thereof and the N-oxide form thereof, wherein $R^3$ is a radical according to any one of Formula (IIIa), (IIIb) or (IIIc)

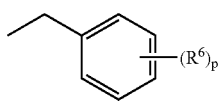

(a)

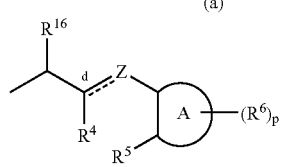

(b)

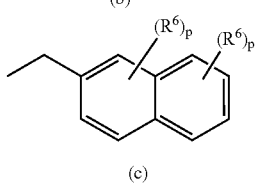

(c)

wherein:

d is a single bond while Z is either a bivalent radical selected from the group of —CH$_2$—, —C(=O)—, —CH(OH)—, —C(=N—OH)—, —CH(alkyl)—, —O—, —S—, —S(=O)—, —NH— and —SH—; or Z is a trivalent CH-moiety that forms a covalent bond with $R^4$ equal to alkyl, such that a cycloalkyl moiety is formed; or d is a double bond while Z is either a trivalent radical of formula =CH— or =C(alkyl)—; or Z is a trivalent CH-moiety that forms a covalent bond with $R^4$ equal to alkyl, such that a cycloalkenyl moiety is formed;

A is a 5- or 6-membered aromatic homocyclic or heterocyclic ring, selected from the group of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;

p is an integer ranging from 0 to 6;

$R^4$ and $R^5$ are each, independently from each other, selected from the group of hydrogen, alkyl, Ar, biphenyl, halo and cyano; or $R^4$ and $R^5$ may be taken together to form a bivalent radical —$R^4$—$R^5$— selected from the group of —CH$_2$—, =CH—, —CH$_2$—CH$_2$—, —CH=CH—, —O—, —NH—, =N—, —S—, —CH$_2$N(-alkyl)—, —N(-alkyl)CH$_2$—, —CH$_2$NH—, —NHCH$_2$—, —CH=N—, —N=CH—, —CH$_2$O— and —OCH$_2$—;

each $R^6$ is independently from each other, selected from the group of hydroxy, amino, nitro, cyano, halo, carboxyl, alkyl, Ar, alkyloxy, Aroxy, alkyl-carbonyloxy, alkyloxycarbonyl, alkylthio, mono- and di(alkyl)amino, alkylcarbonylamino, mono- and di(alkyl)aminocarbonyl, mono- and di(alkyl)aminocarbonyloxy, mono- and di(alkyl)aminoalkyloxy; or two vicinal radicals $R^6$ may be taken together to form a bivalent radical —$R^6$—$R^6$— selected from the group of —CH$_2$—CH$_2$—O—, —O—CH$_2$—CH$_2$—, —O—CH$_2$—C(=O)—, —C(=O)—CH$_2$—O—, —O—CH$_2$—O—, —CH$_2$—O—CH$_2$—, —O—CH$_2$—CH$_2$—O—, —CH=CH—CH=CH—, —CH=CH—CH=N—, —CH=CH—N=CH—, —CH=N—CH=CH—, —N=CH—CH=CH—, —CH$_2$—CH$_2$—CH$_2$—, —CH$_2$—CH$_2$—C(=O)—, —C(=O)—CH$_2$—CH$_2$—, —CH$_2$—C(=O)—CH$_2$— and —CH$_2$—CH$_2$—CH$_2$—CH$_2$—; and $R^{16}$ is selected from the group of hydrogen, alkyl, Ar and Aralkyl.

Preferably, the invention relates to those compounds according to Formula (I), the pharmaceutically acceptable acid or base addition salts thereof, the stereochemically isomeric forms thereof and the N-oxide form thereof, wherein $R^3$ is a radical according to any one of Formula (IIIa), (IIIb) or (IIIc) wherein:

d is a double bond while Z is a trivalent radical of formula =CH— or =C(alkyl)—;

A is phenyl;

p is an integer equal to 0 or 1;

$R^4$ and $R^5$ are each, independently from each other, selected from the group of hydrogen and alkyl; and each $R^6$ is halo; and $R^{16}$ is hydrogen.

More preferably, the invention relates to compounds according to Formula (I), the pharmaceutically acceptable acid or base addition salts thereof, the stereochemically isomeric forms thereof and the N-oxide form thereof, where X=O, one of $R^1$ and $R^2$ is hydrogen, methoxy or ethoxy; m=1; Pir is a radical according to Formula (IIa) wherein n=0; $R^3$ is a radical according to Formula (IIIb) wherein Z is =CH—, d is a double bond, A is a phenyl ring, $R^4$ is methyl and $R^5$ and $R^{16}$ are each hydrogen.

Particularly interesting compounds are those compounds according to Formula (I), the pharmaceutically acceptable acid or base addition salts thereof, the stereochemically isomeric forms thereof and the N-oxide form thereof where $R^1$ is hydrogen or methoxy and $R^2$ is an amine radical $NR^{10}R^{11}$, X=O, m=1; Pir is a radical according to Formula (IIa) wherein n=0; $R^3$ is a radical according to Formula (IIIb) wherein Z is =CH—, d is a double bond, A is a phenyl ring, $R^4$ is methyl and $R^5$ and $R^{16}$ are each hydrogen.

Particularly interesting compounds are those compounds in which A is an unsubstituted phenyl ring or a phenyl ring substituted with a halo atom, in particular with F, Cl or Br.

In the framework of this application, alkyl defines straight or branched saturated hydrocarbon radicals having from 1 to 6 carbon atoms, for example methyl, ethyl, propyl, butyl, 1-methylpropyl, 1,1-dimethylethyl, pentyl, hexyl; or alkyl defines cyclic saturated hydrocarbon radicals having from 3 to 6 carbon atoms, for example cyclopropyl, methylcyclopropyl, cyclobutyl, cyclopentyl and cyclohexyl. Alkyl radicals may be optionally substituted with one or more halo, cyano, oxo, hydroxy, alkyloxy or amino radicals, for example polyhaloalkyl, in particular difluoromethyl and trifluoromethyl.

In the framework of this application, halo is generic to fluoro, chloro, bromo and iodo.

In the framework of this application, alkenyl represents a straight or branched unsaturated hydrocarbon radical having one or more double bonds, for example ethenyl, 1-propenyl, 2-propenyl and 1,3-butanedienyl. Alkenyl radicals may be optionally substituted with one or more halo, cyano, oxo, hydroxy, alkyloxy or amino radicals, for example hydroxyethenyl.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more nitrogens of the piperazinyl radical are N-oxidized.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centres may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centres of known absolute configuration are present in a molecule, an R or S descriptor is assigned (based on Cahn-Ingold-Prelog sequence rule) to the lowest-numbered chiral centre, the reference centre. The configuration of the second stereogenic centre is indicated using relative descriptors [R*,R*] or [R*, S*], where R* is always specified as the reference centre and [R*, R*] indicates centres with the same chirality and [R *,S*] indicates centres of unlike chirality. For example, if the lowest-numbered chiral centre in the molecule has an S configuration and the second centre is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds of Formula (I)) relative to the position of the highest priority substituent on the reference atom is denominated "α", if it is on the same side of the mean plane determined by the ring system, or "β", if it is on the other side of the mean plane determined by the ring system.

Compounds of Formula (I) and some of the intermediates have at least two stereogenic centres in their structure, respectively denoted a and b in Formula (I). Due to the synthetic pathway followed for the synthesis of the tricyclic system, the configuration of those two asymmetric centres a and b is predetermined, so that the relative configuration of centre a is S* and of centre b is R*.

The invention also comprises derivative compounds (usually called "prodrugs") of the pharmacologically-active compounds according to the invention, which are degraded in vivo to yield the compounds according to the invention. Prodrugs are usually (but not always) of lower potency at the target receptor than the compounds to which they are degraded. Prodrugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on prodrugs may be found in Stella, V. J. et al., "Prodrugs", *Drug Delivery Systems,* 1985, pp. 112-176, and *Drugs,* 1985, 29, pp. 455-473.

Prodrugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

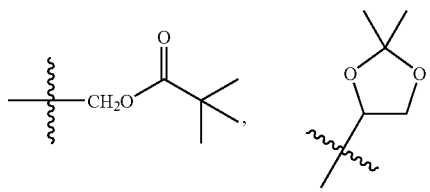

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyse with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds according to the invention, in particular compounds according to Formula (I), the pharmaceutically acceptable acid or base addition salts thereof, the stereochemically isomeric forms thereof and the N-oxide form thereof, have surprisingly been shown to have selective serotonin (5-HT) reuptake inhibitor activity in combination with additional ($\alpha_2$-adrenoceptor antagonist activity and show a strong anti-depressant and/or anxiolytic activity and/or antipsychotic and/or a body weight control activity without being sedative. Also, in view of their selective serotonin (5-HT) reuptake inhibitor as well as $\alpha_2$-adrenoceptor antagonist activity, compounds according to the invention are also suitable for treatment and/or prophylaxis in diseases where either one of the activities alone or the combination of said activities may be of therapeutic use. In particular, the compounds according to the invention may be suitable for treatment and/or prophylaxis in the following diseases:

Central nervous system disorders, including:
Mood disorders, including particularly major depressive disorder, depression with or without psychotic features, catatonic features, melancholic features, atypical features of postpartum onset and, in the case of recurrent episodes, with or without seasonal pattern, dysthymic disorder, bipolar I disorder, bipolar II disorder, cyclothymic disorder, recurrent brief depressive disorder, mixed affective disorder, bipolar disorder not otherwise specified, mood disorder due to a general medical condition, substance-induced mood disorder, mood disorder not otherwise specified, seasonal affective disorder and premenstrual dysphoric disorders.

Anxiety disorders, including panic attack, agoraphobia, panic disorder without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Stress-related disorders associated with depression and/or anxiety, including acute stress reaction, adjustment disorders (brief depressive reaction, prolonged depressive reaction, mixed anxiety and depressive reaction, adjustment disorder with predominant disturbance of other emotions, adjustment disorder with predominant disturbance of conduct, adjustment disorder with mixed disturbance of emotions and conduct, adjustment disorders with other specified predominant symptoms) and other reactions to severe stress.

Dementia, amnesic disorders and cognitive disorders not otherwise specified, especially dementia caused by degenerative disorders, lesions, trauma, infections, vascular disorders, toxins, anoxia, vitamin deficiency or endocrinic disorders, or amnesic disorders caused by alcohol or other causes of thiamin deficiency, bilateral temporal lobe damage due to Herpes simplex encephalitis and other limbic encephalitis, neuronal loss secondary to anoxia/hypoglycemia/severe convulsions and surgery, degenerative disorders, vascular disorders or pathology around ventricle III.

Cognitive disorders due to cognitive impairment resulting from other medical conditions.

Personality disorders, including paranoid personality disorder, schizoid personality disorder, schizotypical personality disorder, antisocial personality disorder, borderline personality disorder, histrionic personality disorder, narcissistic personality disorder, avoidant personality disorder, dependent personality disorder, obsessive-compulsive personality disorder and personality disorder not otherwise specified.

Schizoaffective disorders resulting from various causes, including schizoaffective disorders of the manic type, of the depressive type, of mixed type, paranoid, disorganized, catatonic, undifferentiated and residual schizophrenia, schizophreniform disorder, schizoaffective disorder, delusional disorder, brief psychotic disorder, shared psychotic disorder, substance-induced psychotic disorder and psychotic disorder not otherwise specified.

Akinesia, akinetic-rigid syndromes, dyskinesia and medication-induced parkinsonism, Gilles de la Tourette syndrome and its symptoms, tremor, chorea, myoclonus, tics and dystonia.

Attention-deficit/hyperactivity disorder (ADHD).

Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification.

Dementia of the Alzheimer's type, with early or late onset, with depressed mood.

Behavioral disturbances and conduct disorders in dementia and the mentally retarded, including restlessness and agitation.

Extra-pyramidal movement disorders.

Down's syndrome.

Akathisia.

Eating Disorders, including anorexia nervosa, atypical anorexia nervosa, bulimia nervosa, atypical bulimia nervosa, overeating associated with other psychological disturbances, vomiting associated with other psychological disturbances and non-specified eating disorders.

AIDS-associated dementia.

Chronic pain conditions, including neuropathic pain, inflammatory pain, cancer pain and post-operative pain following surgery, including dental surgery. These indications might also include acute pain, skeletal muscle pain, low back pain, upper extremity pain, fibromyalgia and myofascial pain syndromes, orofascial pain, abdominal pain, phantom pain, tic douloureux and atypical face pain, nerve root damage and arachnoiditis, geriatric pain, central pain and inflammatory pain.

Neurodegenerative diseases, including Alzheimer's disease, Huntington's chorea, Creutzfeld-Jacob disease, Pick's disease, demyelinating disorders, such as multiple sclerosis and ALS, other neuropathies and neuralgia, multiple sclerosis, amyotropical lateral sclerosis, stroke and head trauma.

Addiction disorders, including:

Substance dependence or abuse with or without physiological dependence, particularly where the substance is alcohol, amphetamines, amphetamine-like substances, caffeine, cannabis, cocaine, hallucinogens, inhalants, nicotine, opioids, phencyclidine, phencyclidine-like compounds, sedative-hypnotics, benzodiazepines and/or other substances, particularly useful for treating withdrawal from the above substances and alcohol withdrawal delirium.

Mood disorders induced particularly by alcohol, amphetamines, caffeine, cannabis, cocaine, hallucinogens, inhalants, nicotine, opioids, phencyclidine, sedatives, hypnotics, anxiolitics and other substances.

Anxiety disorders induced particularly by alcohol, amphetamines, caffeine, cannabis, cocaine, hallucinogens, inhalants, nicotine, opioids, phencyclidine, sedatives, hypnotics, anxiolitics and other substances and adjustment disorders with anxiety.

Smoking cessation.

Body weight control, including obesity.

Sleep disorders and disturbances, including:

Dyssomnias and/or parasomnias as primary sleep disorders, sleep disorders related to another mental disorder, sleep disorder due to a general medical condition and substance-induced sleep disorder.

Circadian rhythms disorders.

Improving the quality of sleep.

Sexual dysfunction, including sexual desire disorders, sexual arousal disorders, orgasmic disorders, sexual pain disorders, sexual dysfunction due to a general medical condition, substance-induced sexual dysfunction and sexual dysfunction not otherwise specified.

The present invention thus also relates to compounds of Formula (I), the pharmaceutically acceptable acid or base addition salts thereof, the stereochemically isomeric forms thereof, the N-oxide form thereof, as well as the pro-drugs thereof for use as a medicine, in particular for treating depression, anxiety, movement disorders, psychosis, Parkinson's disease and body weight disorders.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof and the N-oxide form thereof or a prodrug as defined above.

The compounds of the invention, in particular the compounds according to Formula (I), the pharmaceutically acceptable acid or base addition salts thereof, the stereochemically isomeric forms thereof and the N-oxide form thereof and the prodrugs, or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The compounds according to the invention may also be suitable as add-on treatment and/or prophylaxis in the above listed diseases in combination with any combination of compounds selected from the group of antidepressants, anxiolytics, antipsychotics and/or anti-Parkinson's disease drugs which are currently available or in development or which will become available in the future, to improve efficacy and/or onset of action. This is evaluated in rodent models in which antidepressants, anxiolytics, antipsychotics and/or anti-Parkinson's disease drugs are shown to be active. For example, compounds are evaluated in combination with antidepressants, anxiolytics, antipsychotics and/or anti-Parkinson's disease drugs for attenuation of stress-induced hyperthermia.

The invention therefore also relates to a pharmaceutical composition comprising the compounds according to the invention, in particular the compounds according to Formula (I), the pharmaceutically acceptable acid or base addition salts thereof, the stereochemically isomeric forms thereof and the N-oxide form thereof, and the prodrugs and one or more other compounds selected from the group of antidepressants, anxiolytics, antipsychotics and/or anti-Parkinson's disease drugs.

The invention further relates to a process for making a pharmaceutical composition comprising mixing a compound according to the invention, in particular the compounds according to Formula (I), the pharmaceutically acceptable acid or base addition salts thereof, the stereochemically isomeric forms thereof and the N-oxide form thereof, and the prodrugs, or any subgroup thereof and a compound selected from the group of antidepressants, anxiolytics, antipsychotics and anti-Parkinson's disease drugs and a pharmaceutically acceptable carrier.

The invention also relates to the use of a compound according to the invention, in particular the compounds according to Formula (I), the pharmaceutically acceptable acid or base addition salts thereof, the stereochemically isomeric forms thereof and the N-oxide form thereof, and the prodrugs, for the manufacture of a medicament for treating depression, anxiety, movement disorders, psychosis, schizophrenia and body weight disorders.

In vitro receptor and neurotransmitter transporter binding and signal-transduction studies can be used to evaluate the $\alpha_2$-adrenoceptor antagonism activity and serotonin (5-HT) reuptake inhibitor activity of the present compounds. As indices for central penetration and potency to block the $\alpha_2$-adrenoceptors and serotonin transporters, respectively, ex vivo $\alpha_2$-adrenoceptor and serotonin transporter occupancy can be used. As indices of $\alpha_2$-adrenoceptor antagonism in vivo, the reversal of the loss of righting reflex, observed in rats after subcutaneous injection or oral dosage of the compound before intravenous medetomidine administration in rats can be used (medetomidine-test). As indices of serotonin (5-HT) reuptake inhibition activity, the inhibition of head-twitches and excitation in rats, observed after subcutaneous injection or oral dosage of the compound before subcutaneous p-chloroamphetamine administration in rats can be used (pCA-test).

The compounds according to the invention can generally be prepared by a succession of steps, each of which is known to the skilled person.

In particular, the compounds according to Formula (I) can be prepared by a reaction (generally called a nucleophilic aromatic substitution reaction) with an amine of Formula (V) on an intermediate compound according to Formula (IV),

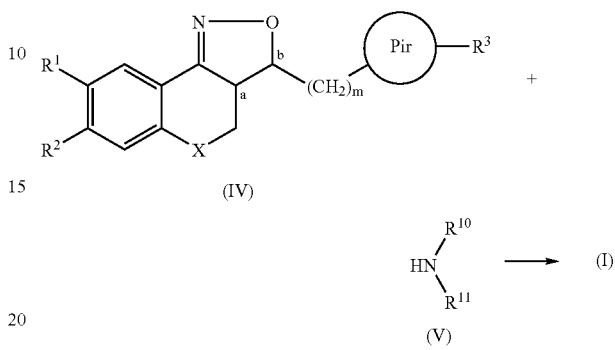

wherein all variables, except for $R^1$ and $R^2$, have the same meaning as in Formula (I), at least one of $R^1$ and $R^2$ is an halogen and at most one of $R^1$ and $R^2$ is selected from the group of hydrogen, hydroxy, cyano, halo, $OSO_2H$, $OSO_2CH_3$, $N-R^{10}R^{11}$, alkyloxy, alkyloxyalkyloxy, alkyloxyalkyloxyalkyloxy, tetrahydrofuranyloxy, alkylcarbonyloxy, alkylthio, alkyloxyalkylcarbonyloxy, pyridinylcarbonyloxy, alkylcarbonyloxyalkyloxy, alkyloxycarbonyloxy, alkenyloxy, alkenylcarbonyloxy and mono- or di(alkyl)aminoalkyloxy.

Such a reaction can also be formulated either as

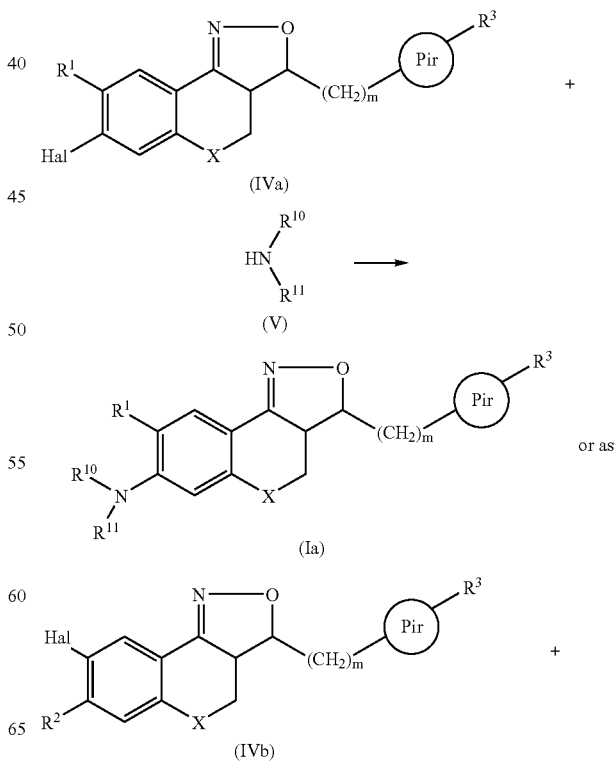

or as

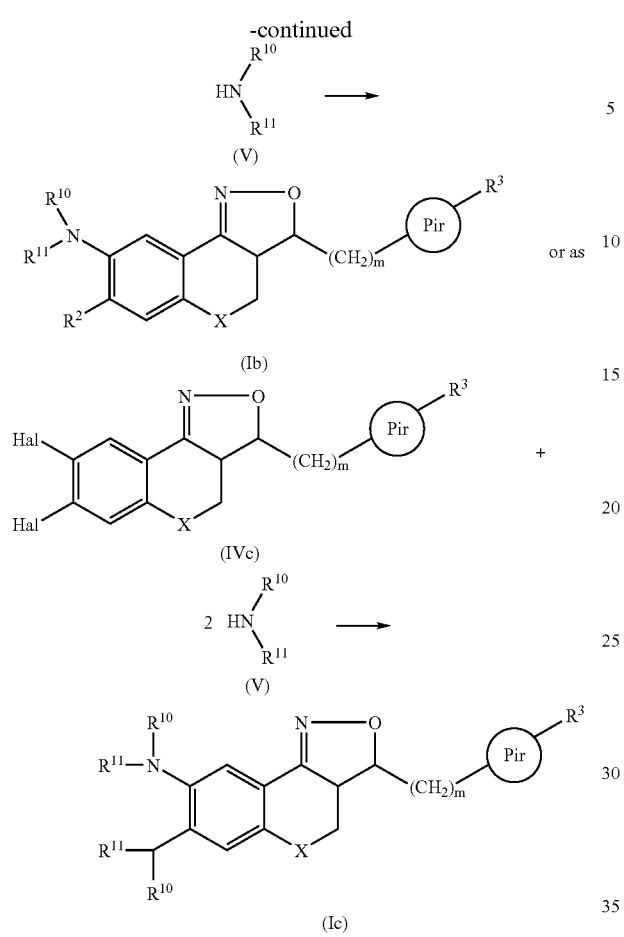

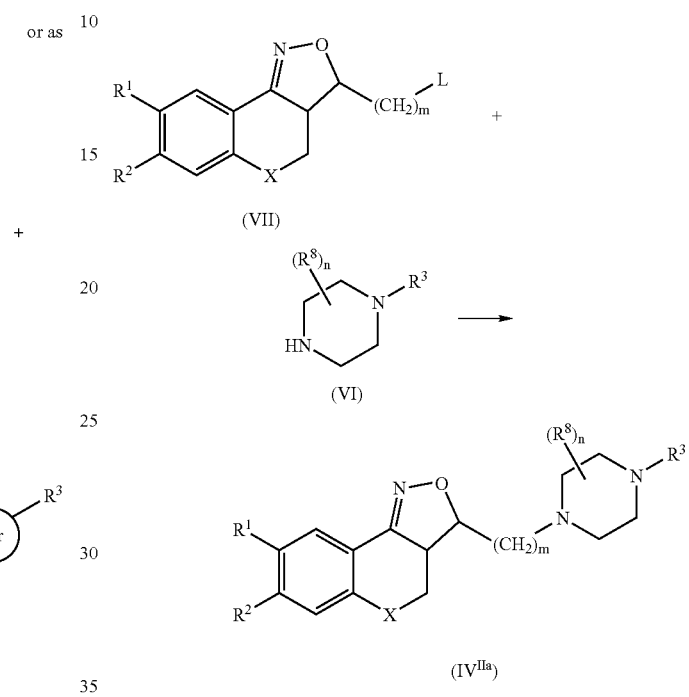

Said reaction may be carried out in a reaction inert solvent such as pyridine, in the presence of a suitabele base such as KF and at a temperature between room and reflux temperature.

The substituents $R^1$ and $R^2$ may be changed or interconverted into each other by methods well known in the art, such as demethylation, acylation, esterification, amination and amidation. In particular, some of the reactions known to apply for the reduction of secondary amines can be applied, for instance the reduction of a benzylamine radical to the corresponding amine-radical using for instance HBr and acetic acid or the synthesis of a secondary amine radical from a primary amine radical by the reaction with an isocyanate or an acylhalide in an appropriate reaction-inert solvent, such as trichloromethane in the presence of a suitable base, such as triethylamine.

The starting materials and some of the intermediate compounds are compounds that are either commercially available or may be prepared according to conventional reaction procedures generally known in the art.

The intermediate compounds, in particular the intermediate compounds according to Formula (IV), more in particular according to Formula (IVa), (IVb) and (IVc) can be prepared according to various ways.

In particular, the compounds according to Formula (IV$^{IIa}$), i.e. compounds according to Formula (IV) with a Pir-radical according to Formula (IIa) can be prepared by a nucleophilic substitution reaction with a substituted piperazine according to Formula (VI) on an intermediate compound of Formula (VII). These reactions may be carried out in a reaction inert solvent such as dioxane, methylisobutylketone or N,N'-dimethylformamide, in the presence of a suitable base such as potassium carbonate, sodium carbonate or triethylamine, or even without a base, using in this latter case excess of reagent of Formula (VI). Convenient reaction temperatures range between 100° C. and 150° C.

In the intermediate compound of Formula (VII), L represents any suitable reactive leaving group, in particular halo, such as chloro, bromo or iodo or sulfonyloxy, such as methylsulphonyloxy or 4-methylbenzenesulfonyloxy.

The compounds according to Formula (IV$^{IIa}$) can also be prepared by a 2-step reaction scheme in which an intermediate compound of Formula (VII) is first reacted (step 1) with a substituted piperazine according to Formula (VIII) after which the $R^3$-radical is introduced into the resulting intermediate compound of Formula (IX) (step 2). Reaction conditions are similar to those described above for intermediate compounds of Formula (IV$^{IIa}$).

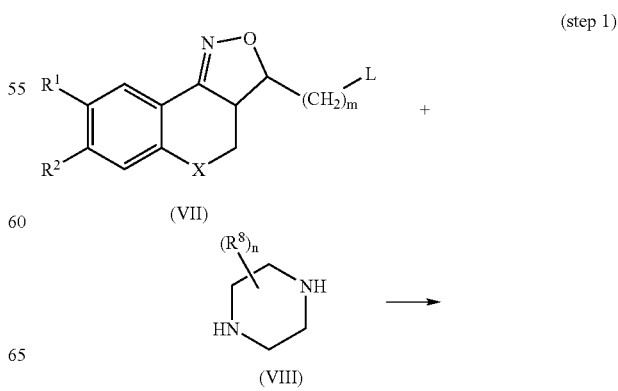

(step 1)

-continued

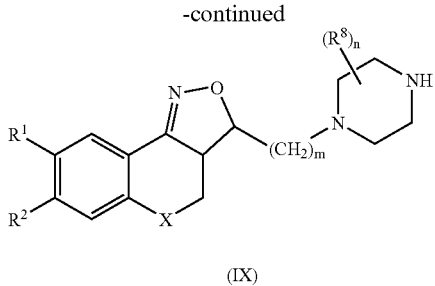

(IX)

In intermediate compound of Formula (VII), L represents any suitable reactive leaving group, in particular halo, such as chloro, bromo or iodo or sulfonyloxy, such as methylsulphonyloxy or 4-methylbenzenesulfonyloxy.

One of the nitrogen functions of the substituted piperazine of Formula (VIII) may also be protected, e.g. by a tert-butyloxycarbonyl-group.

(step 2)

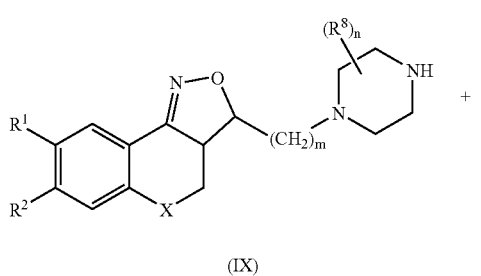

(IX)

L—R³
(X)

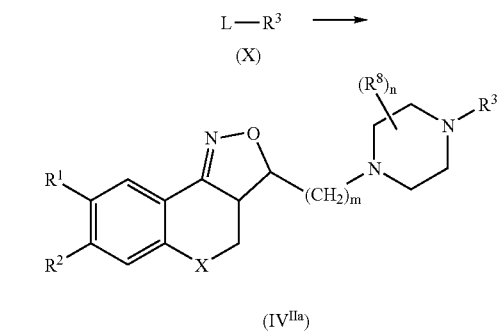

(IV$^{IIa}$)

In the compound of Formula (X), L represents any suitable reactive leaving group, in particular halo, such as chloro, bromo or iodo or sulfonyloxy, such as methylsulphonyloxy or 4-methylbenzenesulfonyloxy. Also, R³–CHO may be used instead of a compound of Formula (X) wherin R³ has the same meaning as in Formula (I).

The compounds according to Formula (IV$^{IIa}$) can also be prepared by a 2-step reaction scheme in which an intermediate of Formula (IX) is reacted with an acid according to Formula (XI) (step 1), followed by a subsequent reduction of the carbonyl-function of the intermediate compound of Formula (XII) (step 2). Reactions of step 1 may be carried out in a reaction inert solvent, such as chloroform, dichloromethane, tetrahydrofuran, dimethylformamide or a mixture thereof, using any of methods known to a person skilled in the art using condensation reagents such as 1,1'-carbonyldiimidazole, N,N'-dicyclohexylcarbodiimide or by previous transformation of carboxylic acid of Formula (XI) into its corresponding acid chloride. Reactions shown in step 2 can be performed using a suitable reducing agent, such as lithium-aluminum hydride or aluminum hydride, in a suitable solvent, for example tetrahydrofuran. Generally, these reactions are run at a temperature ranging between −20° C. and room temperature.

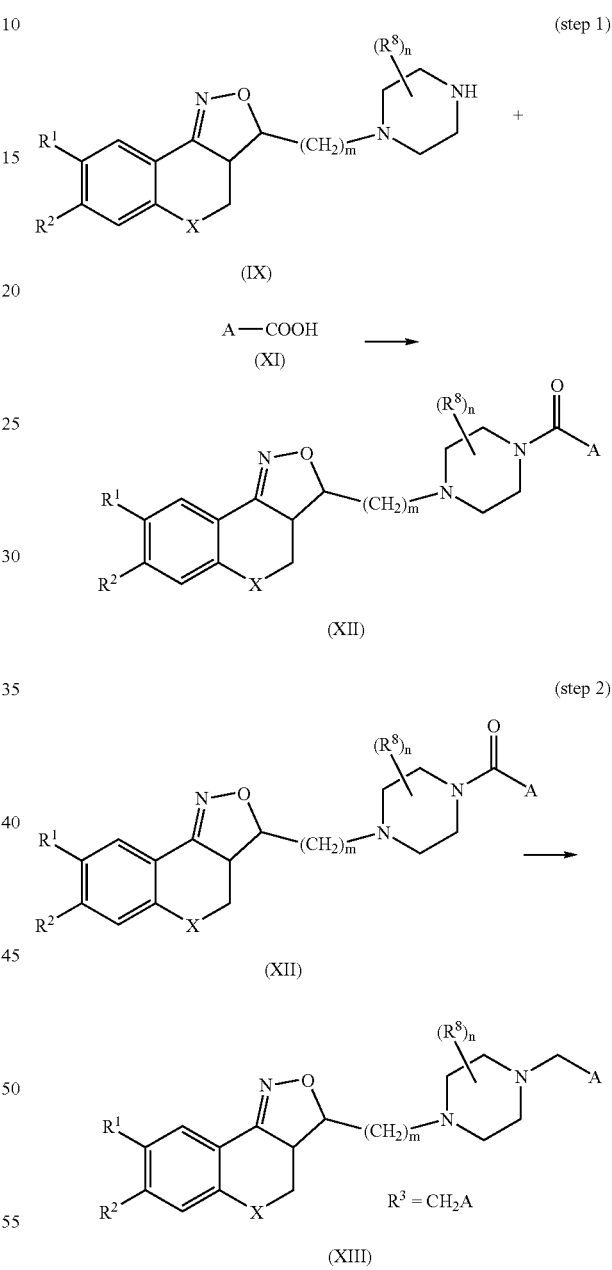

In the intermediate compounds of Formula (XI), (XII) and (XIII), the A-group represents an optionally substituted aromatic homocyclic or heterocyclic ring system including a partially or completely hydrogenated hydrocarbon chain of maximum 5 atoms long of which one or more carbon atoms may be replaced by one or more atoms selected from the group of oxygen, nitrogen and sulphur, with which the ring system is attached to the Pir radical that has been defined above.

Intermediate compounds of Formula (VII) in which X=O may be prepared according to the following reaction scheme:

(step 1a)

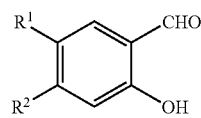

(XIV)

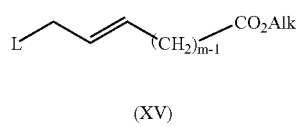

(XV)

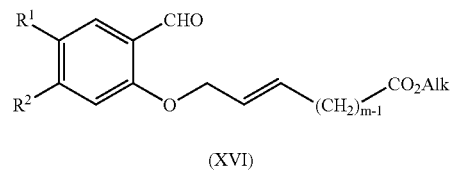

(XVI)

In intermediate compound of Formula (XV), L represents any suitable reactive leaving group, in particular halo, such as chloro, bromo or iodo or sulfonyloxy, such as methylsulphonyloxy or 4-methylbenzenesulfonyloxy. Furthermore, Alk in intermediate compound of Formula (XV) represents any $C_{1-6}$ alkyl-group, in particular an ethyl-group and m is defined as in Formula (I).

Intermediates according to Formula (VII) in which X=NH may also be prepared in an equivalent manner according to above step 1a, provided that the intermediate compound of Formula (XIV) is replaced by its amine-analog of Formula (XVII), preferably with the amine group protected with e.g. a $COCF_3$— group. The alkylation step may be carried out in a reaction inert solvent, for example, tetrahydrofuran or dimethylformamide, in the presence of a strong base, such as sodium or potassium hydride, and the addition of a crown-ether, such as 18-crown-6 or 15-crown-5. Convenient reaction temperatures range between room temperature and 60° C., (step 1b)

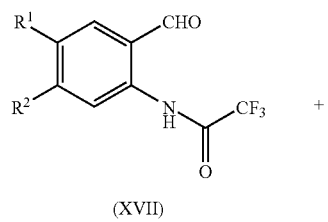

(XVII)

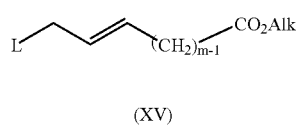

(XV)

-continued

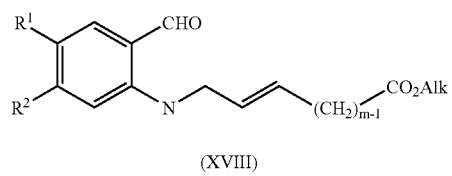

(XVIII)

Intermediates of Formula (XVIII) are converted to oximes of Formula (XIX) using art-known techniques, such as using hydroxylamine hydrochloride in the presence of $NaHCO_3$ or pyridine in a reaction inert solvent, for example ethanol (step 2).

(step 2)

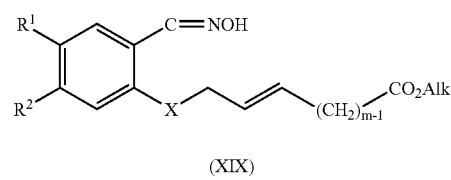

(XVIII)

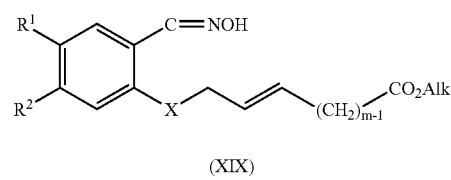

(XIX)

Intermediate compounds of Formula (XIX) are oxidized to their nitril oxides and undergoes in situ an intramolecular cycloaddition, yielding intermediate compounds of Formula (XX). This oxidation can be carried out using a sodium hypochlorite solution in the presence of triethylamine in an inert solvent such as dichloromethane at room temperature. Oxidation can also be performed using Chloramine-T (N-chloro-4-methyl-benzenesulfonamide, sodium salt), stirring and heating in a solvent such as refluxing ethanol. At this stage the two stereocentres a and b of Formula (IV) are formed.

(step 3)

(XIX)

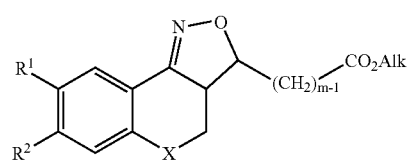

(XX)

Preparation of an intermediate compound of Formula (XXI) can be achieved using procedures known in the art, for instance by reduction of the carbonyl compound of Formula (XX) in the presence of a suitable reducing agent, for example, sodiumborohydride in a suitable solvent, such as water, an alcohol, tetrahydrofuran or a mixture thereof, generally at room temperature.

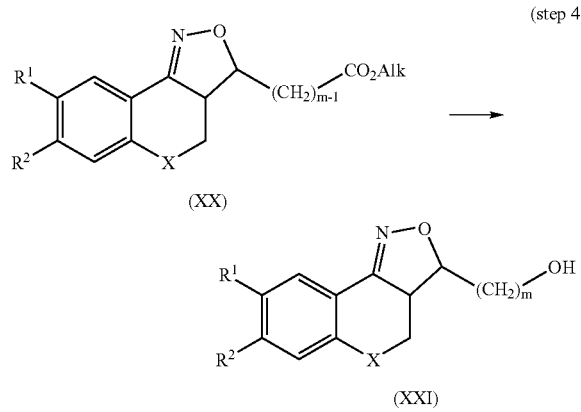

The intermediate compound of Formula (VII) can be prepared from intermediate compound of Formula (XXI) using standard techniques. Thus, reaction with methanesulfonyl chloride or 4-methylbenzenesulfonyl chloride in the presence of a base, such as triethylamine, in a reaction inert solvent, for example dichloromethane, at reaction temperatures ranging between 0° C. and room temperature, yields the corresponding sulfonyloxy derivative intermediate compound of Formula (VII). The corresponding halo-derivative can also be prepared, e.g. treating intermediate compound of Formula (XXI) with triphenylphosphine, in the presence of tetrachloromethane, in a reaction inert solvent, such as tetrahydrofuran, stirring and refluxing the mixture.

It is evident that in the foregoing and in the following reactions, the reaction products may be isolated from the reaction medium and, if necessary, further purified according to methodologies generally known in the art such as extraction, crystallization and chromatography. It is further evident that reaction products that exist in more than one enantiomeric form, may be isolated from their mixture by known techniques, in particular preparative chromatography, such as preparative HPLC. Typically, intermediate compounds (VII) and (IV) and final compounds according to Formula (I) may be separated into their enantiomeric forms.

Compounds according to the invention in which $X=CH_2$ may be prepared according to the following reaction scheme (Scheme 1) in which an intermediate compound according to Formula (VI) is first N-alkylated with a dihaloderivative of Formula (XXII) using standard techniques, in the presence or absence of a base and in an inert reaction solvent, such as chloroform, dichloromethane or 1,2-dichloroethane, and at reaction temperatures ranging between room temperature and 80° C., yielding an intermediate compound of Formula (XXIII). An aldehyde of Formula (XXIV) is reacted with tert-butylamine (XXV) in an aprotic solvent such as toluene, stirring and heating at reflux temperature with removal of water using a standard device, such as a Dean-Stark water separator, yielding an imine of Formula (XXVI). C-alkylation of intermediate compound of Formula (XXVI) with intermediate compound of Formula (XXIII) can be achieved in the presence of an alkyl-lithium derivative, such as n-butyllithium, under an inert atmosphere and in a dry inert solvent, such as tetrahydrofuran, at low temperatures ranging between −78° C. and 0° C., yielding an intermediate compound of Formula (XXVII). The intermediate compound of Formula (XXVIII) may be prepared by reaction of intermediate compound of Formula (XXVII) with hydroxylamine, in the presence of a base such as sodium bicarbonate, in a solvent such as a lower alkyl-alcohol like ethanol, generally at room temperature. Finally, the oxidation of the oxime derivative of Formula (XXVIII) to its nitril oxide and subsequent in situ cycloaddition to give an intermediate compound of Formula (XXIX), may be achieved by similar standard techniques such as those described above for intermediate compound of Formula (XIX) to give intermediate compounds of Formula (XX).

Scheme 1

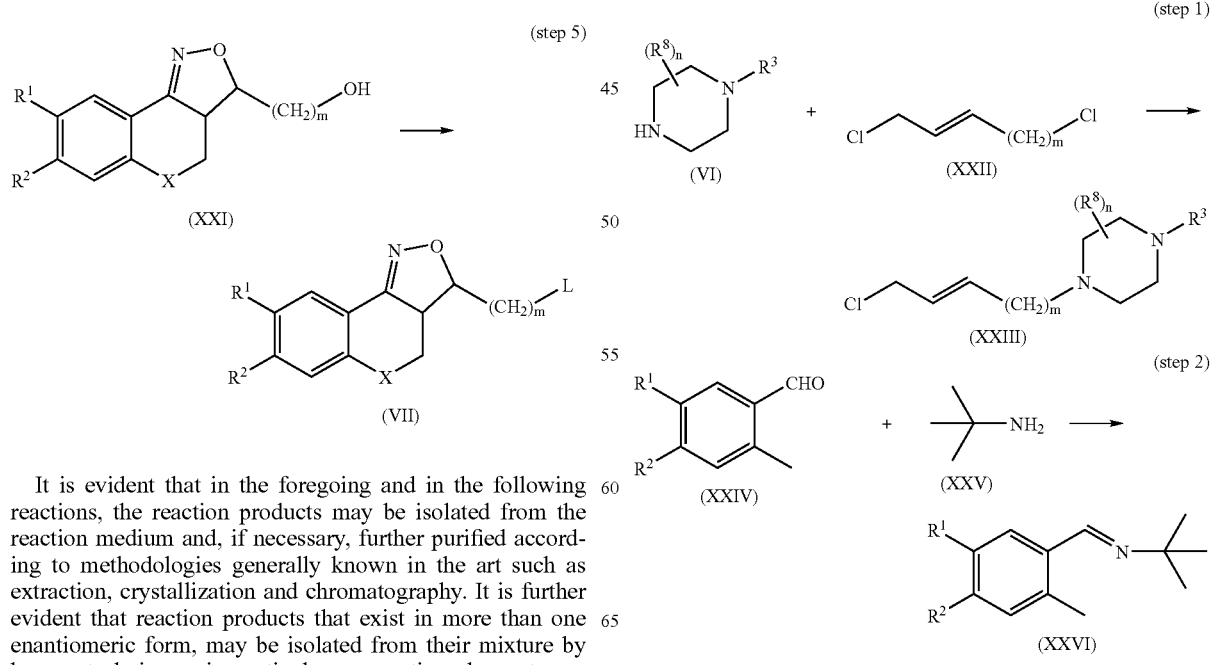

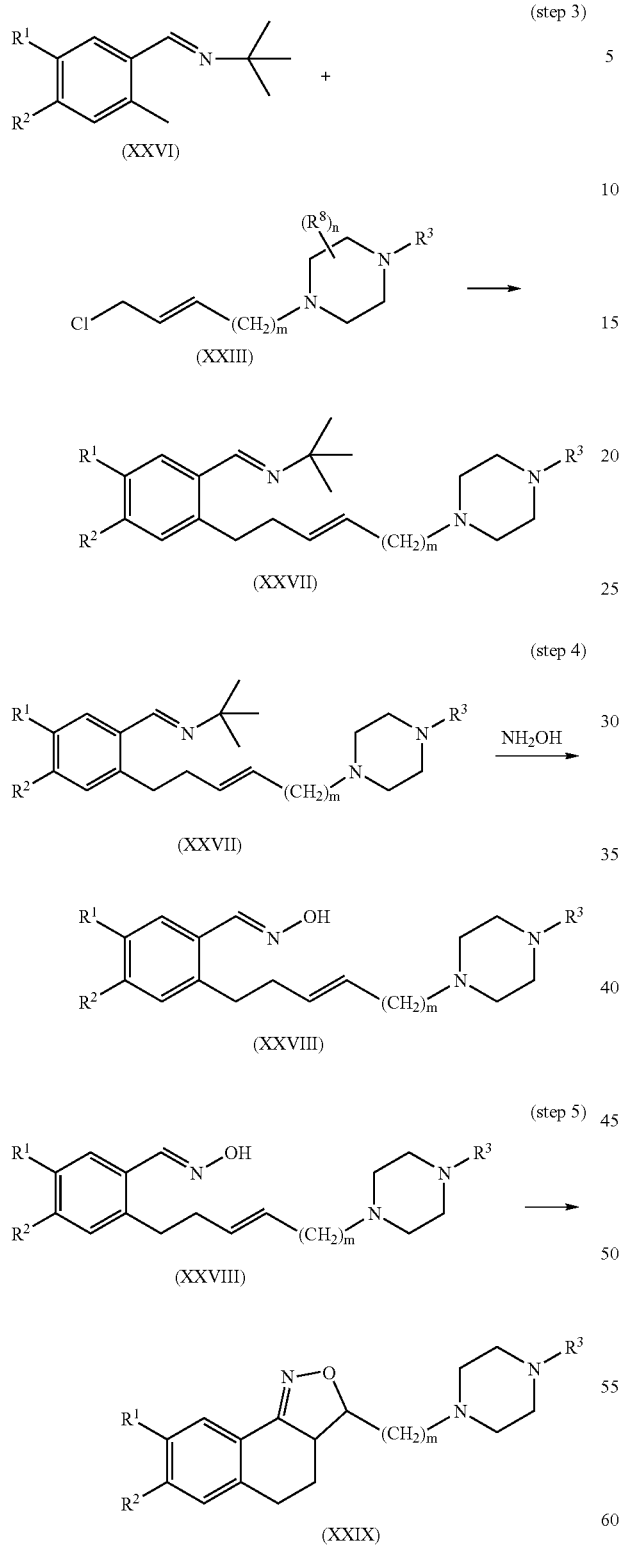

It is evident that the reaction steps disclosed above may be adapted to the specific reaction products. The reaction steps disclosed may be performed in any way known to the skilled person, including in solution or as solid phase reactions, the latter during which the reaction products are bound to a resin material and are—in a final cleavage step—released from the resin material. Examples of such embodiments and adaptations have been disclosed by way of the Examples further in this application.

The following examples illustrate the present invention without being limited thereto.

EXPERIMENTAL PART

The carbon ring numbering system for the compounds according to Formula (I) used in this application is as follows:

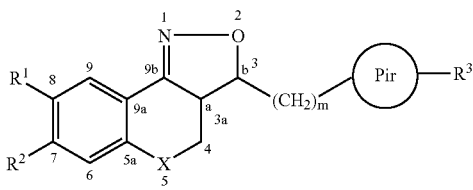

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The stereogenic centres a and b in compounds of Formula (I) have respectively the ring numbers 3a and 3.

Hereinafter, "DMF" is defined as N,N-dimethylformamide, "DIPE" is defined as diisopropyl ether, and "THF" is defined as tetrahydrofurane.

A. Preparation of the Intermediate Compounds

EXAMPLE A.1 a. Preparation of Intermediate Compound 1

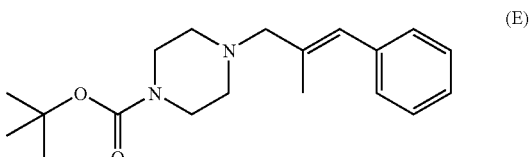

A mixture of (3-chloro-2-methyl-1-propenyl)benzeen (0.0506 mol), 1,1-dimethylethyl 1-piperazinecarboxylate (0.076 mol) and NaHCO₃ (0.0506 mol) in CHCl₃ (150 ml) was stirred and refluxed for 9 hours. The reaction mixture was treated with water and this mixture was extracted with CH₂Cl₂. The residue was purified by short open column chromatography over silica gel (eluent: CH₂Cl₂/CH₃OH 99/1). The pure fractions were collected and the solvent was evaporated. Yield: 16.7 g of intermediate compound 1 (98%).

b. Preparation of Intermediate Compound 2

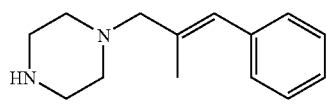 (E)

Trifluoroacetic acid (81 ml) was added dropwise to a solution of intermediate compound 1 (0.0496 mol) in CH$_2$Cl$_2$ (350 ml) and the resulting reaction mixture was stirred for 4 hours at room temperature. The reaction mixture was cooled and alkalized with 50% NaOH. This mixture was extracted and the organic solvent was vaporated. Yield: 9.6 g of intermediate compound 2.

Example A.2 a. Preparation of Intermediate Compound 3

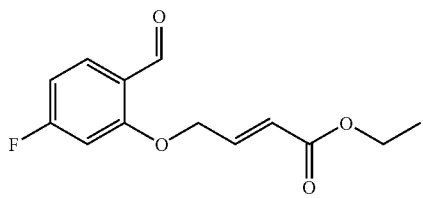 (E)

K$_2$CO$_3$ (0.0265 mol) and ethyl (E)-4-bromo-2-butenoate (0.02145 mol) were added to a solution of 4-fluoro-2-hydroxybenzaldehyde (0.0143 mol) in DMF (16 ml), stirred at 0° C. The reaction mixture was stirred for 5 hours at room temperature. Water was added and this mixture was extracted with CH$_2$Cl$_2$. The separated organic layer was dried (Na$_2$SO$_4$), filtered and the solvent evaporated. The residue was purified by short open column chromatography over silica gel (eluent: CH$_2$Cl$_2$/hexane 1/1 and 2/1). The desired fractions were collected and the solvent was evaporated. Yield: 3.47 g of intermediate compound 3.

b. Preparation of Intermediate Compound 4

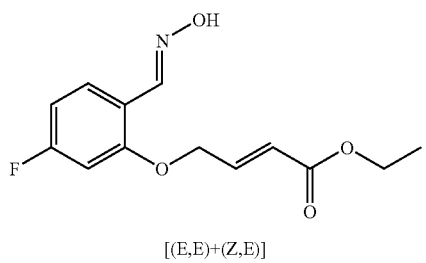
[(E,E)+(Z,E)]

NaOAc (0.0207 mol) and hydroxylamine (0.0165 mol) were added to a solution of intermediate compound 3 (0.0138 mol) in ethanol (35 ml), stirred at 0° C. The reaction mixture was stirred for 2 hours at 0° C. Then, CH$_2$Cl$_2$ and water were added. The mixture was neutralized with a saturated aqueous NaHCO$_3$ solution. The organic layer was separated, dried (Na$_2$SO$_4$), filtered and the solvent was evaporated. Yield: 4.65 g intermediate compound 4.

c. Preparation of Intermediate Compound 5

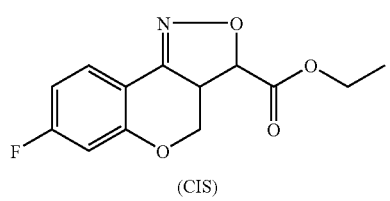
(CIS)

NaClO, 4% (0.0348 mol) was added dropwise to a solution of intermediate compound 4 (0.0174 mol) in CH$_2$Cl$_2$ (70 ml), at 0° C. The reaction mixture was stirred for 2 hours at room temperature. Et$_3$N (0.0261 mol) was added dropwise at 0° C. and the resulting reaction mixture was stirred for 24 hours at room temperature. The organic layer was separated, dried (Na$_2$SO$_4$), filtered and the solvent was evaporated. The residue was purified by short open column chromatography over silica gel (eluent: CH$_2$Cl$_2$/EtOAc 100/0, then 90/10). The product fractions were collected and the solvent was evaporated. Yield: 1.2 g of intermediate compound 5 (26%).

d. Preparation of Intermediate Compound 6

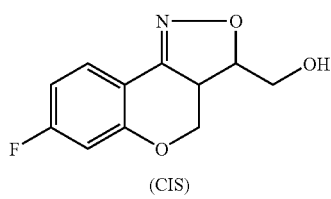
(CIS)

NaBH$_4$ (0.0105 mol) was added portionwise to a solution of intermediate compound 5 (0.0042 mol) in THF (32 ml) and H$_2$O (3 ml), at 0° C. The reaction mixture was stirred for 24 hours at room temperature. A saturated aqueous NH$_4$Cl solution was added and this mixture was extracted with CH$_2$Cl$_2$. The separated organic layer was dried (Na$_2$SO$_4$), filtered and the solvent evaporated. The residue was purified by short open column chromatography over silica gel (eluent: CH$_2$Cl$_2$/EtOAc 9/1 and CH$_2$Cl$_2$/2-propanone 4/1). The desired fractions were collected and the solvent was evaporated. Yield: 0.76 g of intermediate compound 6 (81%).

e. Preparation of Intermediate Compound 7

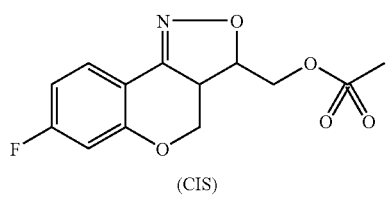

(CIS)

At 0° C., methanesulfonyl chloride (0.003696 mol) was added to a solution of intermediate compound 6 (0.00336 mol) and Et$_3$N (0.00504 mol) in CH$_2$Cl$_2$ (15 ml). The reaction mixture was stirred for 60 minutes at 0° C. CH$_2$Cl$_2$ was added. A saturated aqueous NaHCO$_3$ solution was added. The organic layer was separated, dried (Na$_2$SO$_4$), filtered and the solvent was evaporated. Yield: 0.890 g of intermediate compound 7 (88%).

Example A.3

Preparation of Intermediate Compound 8

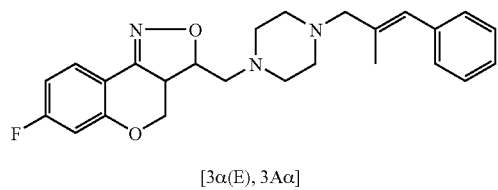

[3α(E), 3Aα]

A mixture of intermediate compound 7 (0.0029 mol), intermediate compound 2 (0.0035 mol) and NaHCO$_3$ (0.0043 mol) in 1,4-dioxane (15 ml) was stirred and refluxed for 24 hours. Water was added. This mixture was extracted with CH$_2$Cl$_2$. The separated organic layer was dried (Na$_2$SO$_4$), filtered and the solvent evaporated. The residue was purified by short open column chromatography over silica gel (eluent: CH$_2$Cl$_2$/EtOAc 9/1, then pure EtOAc). The desired fractions were collected and the solvent was evaporated. The residue was washed with DIPE, then dried. Yield: 0.170 g of intermediate compound 8 (14%).

EXAMPLE A.4

Preparation of Intermediate Compound 13

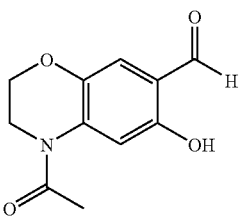

A mixture of 4-acetyl-3,4-dihydro-2H-1,4-benzoxazin-6-ol (0.085 mol), MgCl$_2$ (0.1278 mol), Et$_3$N (0.3197 mol) and CH$_2$O (1.023 mol) in CH$_3$CN (320 ml) was stirred at reflux overnight. The crude reaction was washed with HCl (5%) and extracted with AcOEt. The organic layer was dried over Na$_2$SO$_4$, filtered and evaporated till dryness. The residue was purified by open column chromatography with CH$_2$Cl$_2$ and CH$_2$Cl$_2$:MeOH (1, 2, 4, 10%) as eluents. Yielding 1.13 g of intermediate compound 13 and 14.99 g of a mixture of starting material and expected product. The reaction was repeated with this mixture (0.077 mol), MgCl$_2$ (0.1164 mol), Et$_3$N (0.2909 mol) and CH$_2$O (0.5237 mol) in CH$_3$CN (320 ml). It was purified by open column chromatography with CH$_2$Cl$_2$:MeOH (1, 2, 4, 10%) as eluents. Yield: 9.34 g of intermediate compound 13. Total yielding: 10.47 g of intermediate compound 13 (55%).

B. Preparation of the Final Compounds

Example B.1

Preparation of Final Compound 1

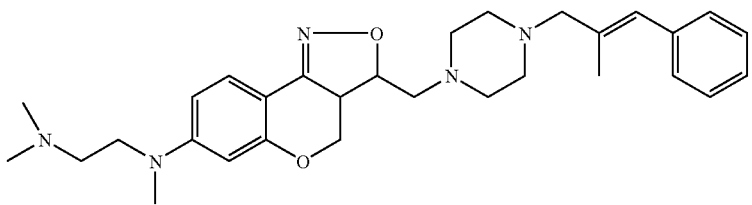

[3α(E), 3Aα]

N,N,N'-trimethyl-1,2-ethanediamine (0.0028469 mol) was added to a solution of intermediate compound 8 (prepared according to A.3) (0.0002372 mol) in pyridine (2 ml), stirred under N$_2$ atmosphere. The reaction mixture was stirred and refluxed for 24 hours in a sealed tube. More N,N,N'-trimethyl-1,2-ethanediamine (0.0028469 mol) was added and the reaction mixture was stirred for 3 days at 120°

C. The solvent was evaporated. The residue was purified by short open column chromatography over silica gel (eluent: CH$_2$Cl$_2$/CH$_3$OH 98/2 and 95/5). The product fractions were collected and the solvent was evaporated. Yield: 0.090 g (76%, free base). The residue was dissolved in 2-propanol and converted into the hydrochloric acid salt (1:2) with HCl/2-propanol. The precipitate was filtered off and dried. Yield: 0.045 g of final compound 1 (33%).

Example B.2

Preparation of Final Compound 2

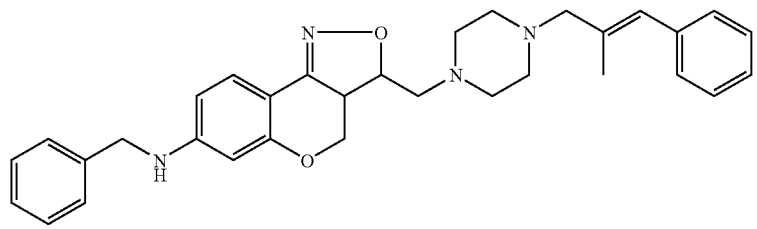

[3α(E), 3Aα]

A mixture of intermediate compound 8 (prepared according to A.3) (0.0024 mol), benzenemethanamine (0.0288 mol) and KF (0.0024 mol) was heated for 5 days at 150° C. in a sealed tube. More benzenemethanamine (0.0288 mol) was added and the reaction mixture was heated at 150° C. for 18 hours. Water was added. This mixture was extracted with CH$_2$Cl$_2$. The separated organic layer was dried (Na$_2$SO$_4$), filtered and the solvent evaporated. The residue was purified by short open column chromatography over silica gel (eluent: CH$_2$Cl$_2$/EtOAc 2/1). The product fractions were collected and the solvent was evaporated. The residue was washed with DIPE, then dried. Yield: 0.890 g of final compound 2 (73%).

Example B.3

Preparation of Final Compound 3

Reaction under N$_2$ atmosphere. A sealed tube was charged with intermediate compound 9,

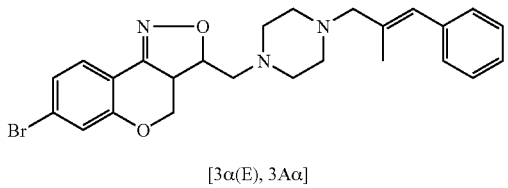

[3α(E), 3Aα]

(prepared according to A.3) (0.0003997 mol), 4-methylbenzenesulfonamide (0.0004796 mol), Pd(OAc)$_2$ (0.000004 mol), Xantphos (0.000006 mol) and Cs$_2$CO$_3$ (0.0005996 mol) in 1,4-dioxane (2 ml), previously de-oxygenated. The reaction mixture was heated to 100° C. for 24 hours. More Pd(OAc)$_2$ (0.000012 mol) and Xantphos (0.000018 mol) were added and the reaction mixture was heated for another 24 hours at 100° C. The reaction mixture was cooled to room temperature, diluted with CH$_2$Cl$_2$, filtered through Celite and the filtrate was evaporated. The residue was purified by Sep-Pak Silica Cartridge chromatography (eluent: CH$_2$Cl$_2$/(CH$_3$OH/NH$_3$) 100/0 and 99/1). The product fractions were collected and the solvent was evaporated. The residue was washed with DIPE, then dried. Yield: 0.100 g of final compound 3 (42%). (Xantphos=Phosphine, 9,9-dimethyl-9H-xanthene-4,5-diyl)bis[diphenyl-=CAS 161265-03-8)

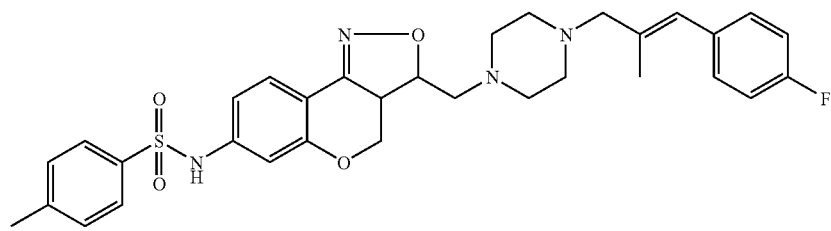

[3α(E), 3Aα]

Example B.4

Preparation of Final Compound 4

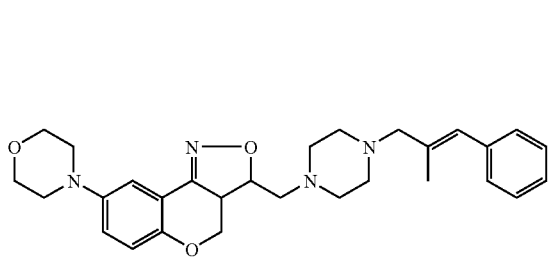

[3α(E), 3Aα]

A mixture of intermediate

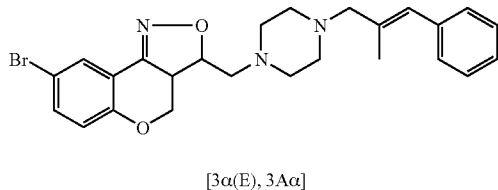

[3α(E), 3Aα]

(prepared according compound 10 to A.3) (0.0003626 mol), Pd(dba)$_2$ (0.00001 mol), tributylphosphine (0.000008 mol), t-BuONa (0.0004945 mol) and morholine (0.0003296 mol) in toluene (q.s.) was stirred in a sealed tube under N$_2$ atmosphere for 24 hours. More morholine (0.0003296 mol) was added and the reaction mixture was stirred for 24 hours at 100° C. Then, water was added and this mixture was extracted with CH$_2$Cl$_2$. The separated organic layer was dried (Na$_2$SO$_4$), filtered and the solvent evaporated. The residue was purified by Sep-Pak Silica Cartridge chromatography (eluent: CH$_2$Cl$_2$/(CH$_3$OH/NH$_3$) 100/0 and 99/1) and washed with DIPE. Yield: 0.040 g of final compound 4 (23%).

Example B.5

Preparation of Final Compound 5

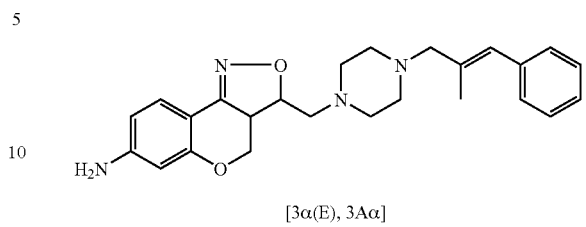

[3α(E), 3Aα]

A mixture of final compound 2 (prepared according to B.2) (0.002949 mol) in HBr (25 ml) and AcOH (50 ml) was warmed at 80° C. for 15 days. The reaction mixture was cooled and treated with Na$_2$CO$_3$ until pH 7-8, extracted with CH$_2$Cl$_2$ and the solvent was evaporated until dry. The residue was purified by short open column chromatography over silica gel (eluent: CH$_2$Cl$_2$/MeOH 99/1; 98/2). The product fractions were collected and the solvent was evaporated. The residue was washed with DIPE. Yield: 0.5 g of final compound 5 (41%).

Example B.6

Preparation of Final Compound 6

[3α(E), 3Aα]

Methylcarbonylchloride (0.0006451 mol) was added to a mixture of final compound 5 (prepared according to B5) (0.0004301 mol) and Et$_3$N (0.0012903 mol) in CHCl$_3$ (7 ml), stirred at 0° C. The reaction mixture was stirred for 2 hours at room temperature. A saturated aqueous NaHCO$_3$ solution was added. The organic layer was separated, dried (Na$_2$SO$_4$), filtered and the solvent was evaporated. The residue was purified by short open column chromatography over silica gel (eluent: CH$_2$Cl$_2$/CH$_3$OH 97/3 and 96/4). The desired fractions were collected and the solvent was evaporated. Yield: 0.100 g of final compound 6 (51%).

Example B.7

Preparation of Final Compound 7

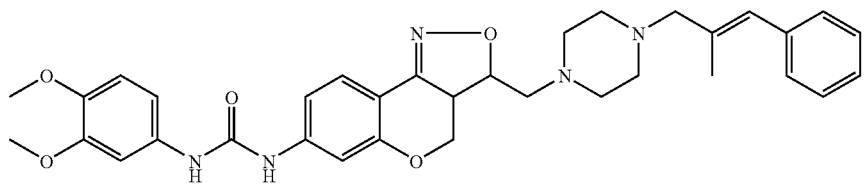

[3α(E), 3Aα]

4-isocyanato-1,2-dimethoxybenzene (0.0007646 mol) was added to a solution of final compound 5 (prepared according to B5) (0.0004779 mol) in THF (3 ml). The reaction mixture was stirred for 24 hours at room temperature. The solvent was evaporated. The residue was purified using Sep-Pak Silica Cartridge chromatography (eluent: CH$_2$Cl$_2$/(CH$_3$OH/NH$_3$) 99/1 and 98/2). The desired fractions were collected and the solvent was evaporated. The residue was washed with DIPE, then dried. Yield: 0.210 g of final compound 7 (73%).

Example B.8

Preparation of Final Compound 8

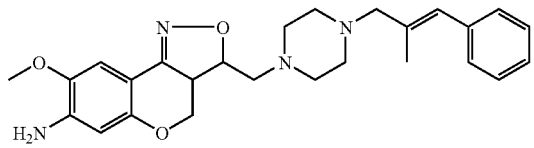

To a solution of intermediate

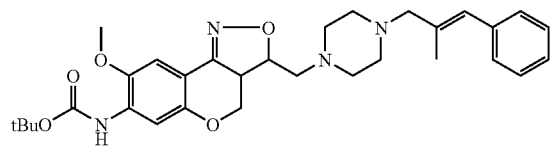

[3α(E), 3Aα]

(prepared according compound 11 to A3) (0.014981 mol) in CH$_2$Cl$_2$ (20 ml), TFA (4 ml) was added dropwisse. The reaction mixture was stirred at room temperature for 5 hours. Then, the mixture was basified with Na$_2$CO$_3$ (saturated solution), extracted with CH$_2$Cl$_2$ and evaporated untill dryness. The solid was washed with DIPE. Yield: 500 mg of final compound 8 (76%).

Example B.9

Preparation of Final Compound 9

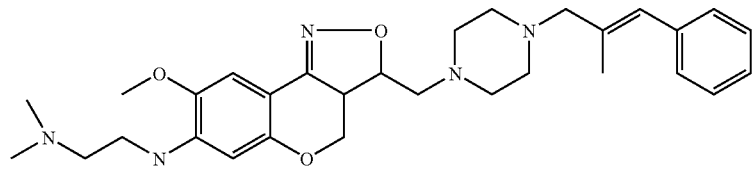

[3RS(E), 3aRS]

Reaction under N$_2$ atmosphere. A sealed tube was charged with Cs$_2$CO$_3$ (0.0008196 mol) that had been finely ground and dried in a dessicator. The tube was then charged with Pd(OAc)$_2$ (0.0391 mmol) and R-BINAP (0.0000527 mol) premixed in de-oxygenated toluene (3 ml).

Then intermediate

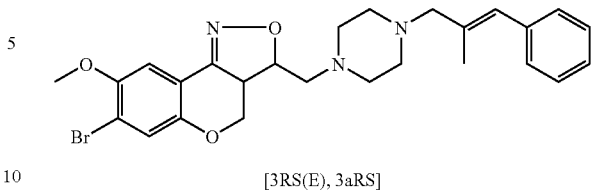

[3RS(E), 3aRS]

(prepared according to A.3) compound 12 (0.0005854 mol) and N,N-dimethyl-1,2-ethanediamine (0.0007025 mol) were added and the mixture was heated to 100° C. for 24 hours. Then, more N,N-dimethyl-1,2-ethanediamine (0.0007025 mol) was added and the mixture was heated to 100° C. for 24 hours. The mixture was cooled to room temperature, diluted with CH$_2$Cl$_2$, filtered over celite and concentrated. The residue was purified by Sep-Pak Silica Cartridge Chromatography (Eluent: CH$_2$Cl$_2$ and CH$_2$Cl$_2$/(CH$_3$OH/NH$_3$) 1% and 2%) and washed with DIPE. Yield: 107 mg of final compound 9 (35%).

Example B.10

Preparation of Final Compound 10

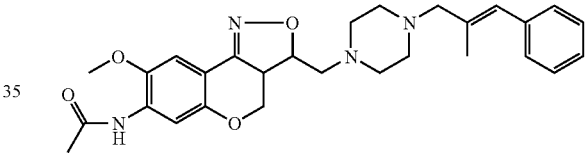

[3α(E), 3aα]

DIEA, polymer-bound was washed with CHCl$_3$ (4 ml). After that, a tube was charged with final compound 8 (prepared according to B.8) (0.0002229 mol), DIEA (0.0004458 mol) in CHCl$_3$ (4 ml) and then acetylchloride (0.0002675 mol) was added at 0° C. The mixture was stirred for 3 hours at room temperature. Then, tris(2-aminoethyl) amine, polymer bound (0.0002229 mol) was added and the mixture was stirred overnight at room temperature. The mixture was filtered, concentrated and the residue was washed with DIPE. Yielding: 75 mg of final compound 10 (69%).

Example B.11

Preparation of Final Compound 11

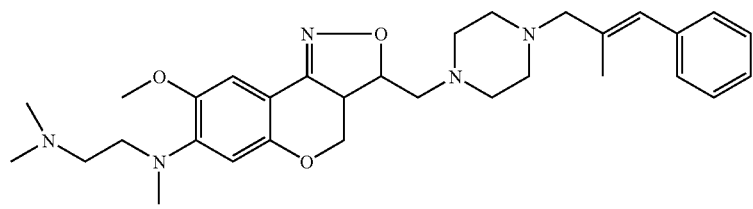

[3α(E), 3aα]

To a mixture of final compound 9 (prepared according to B.9) (0.0002886 mol) and CH₂O (0.0008658 mol) in MeOH (4 ml) was added ZnBr₂ (0.0001443 mol). It was stirred at room temperature for 15 minutes and NaCNBH₃ (0.0004329 mol) was added. The resulting reaction mixture was stirred at reflux for 24 hours. Then, more CH₂O (0.0002886 mol), ZnBr₂ (0.0001443 mol) and NaCNBH₃ (0.0004329 mol) were added and the reaction mixture was stirred at reflux for 24 hours. Then, more CH₂O (0.0002886 mol), ZnBr₂ (0.0001443 mol) and NaCNBH₃ (0.0004329 mol) were added and the mixture was treated with NH₄Cl (10%) and extracted with CH₂Cl₂. The organic layer was separated, dried (Na₂SO₄) and the solvent evaporated. The residue was purified by Sep-Pak Silica Cartridge Chromatography (Eluent: CH₂Cl₂ and CH₂Cl₂/(CH₃OH/NH₃) 1%) and liophilized. Yielding: 28 mg of final compound 11 (18%).

Example B.12

Preparation of Final Compound 12

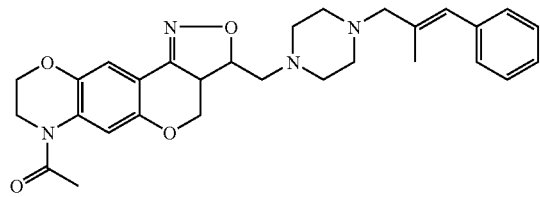

[3RS(E), 3aRS]

A mixture of intermediate

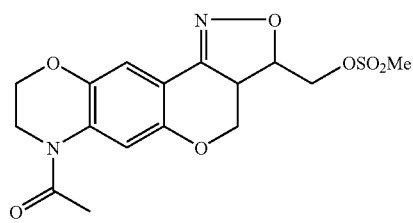

(prepared according to A2.e) compound 14 (0.0099 mol), intermediate compound 2 (prepared according to A1.b) (0.0149 mol), KI (0.0099 mol) and K2CO3 (0.0099 mol) in MIK (35 ml) was stirred at reflux overnight. The crude reaction was evaporated till dryness and the residue was washed with water. It was extracted with AcOEt, dried over Na₂SO₄, filtered and evaporated till dryness. The residue was purified by open column chromatography with CH₂Cl₂: MeOH (4%) as eluent. Yield: 3.1 g of final compound 12 (62%).

Example B.13

Preparation of Final Compound 13

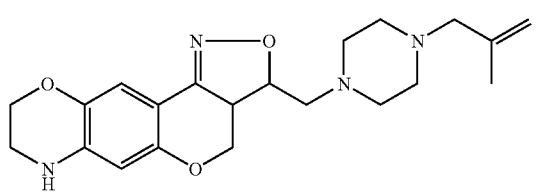

[3α(E), 3aα]

A mixture of final compound 12

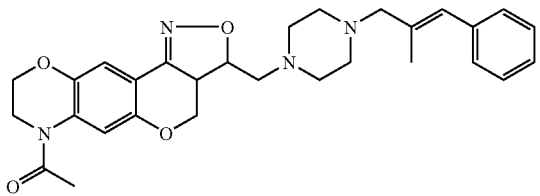

[3RS(E), 3aRS]

(prepared according to B.12) with starting material intermediate compound 13 (prepared according to A.4) instead of 4-fluoro-2-hydroxybenzaldehyde (A2.a)) (0.0046 mol), 15% NaSMe/H₂O (4.41 ml) and MeOH (42 ml) was stirred at reflux for 2 hours and at room temperature overnight. The crude reaction was concentrated under vacuo and the residue was washed with water and extracted with AcOEt. The organic layer was dried over Na₂SO₄, filtered and evaporated till dryness. The residue was purified by open column chromatography with CH₂Cl₂:MeOH (1, 2, 4%) as eluents. Finally, the product was crystallized from DIPE. Yield: 0.85 g of final compound 13 (39%).

Example B.14

Preparation of Final Compound 14

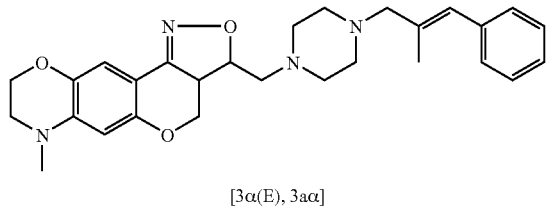

[3α(E), 3aα]

To a mixture of final compound 13 (prepared according to B.13) (0.000217 mol) and CH$_2$O (0.000217 mol) in sodium cyanoborohydride, 95% (0.00032 mol) in a sealed tube, was added ZnBr$_2$ (0.0001 mol). It was stirred at room temperature for 15 minutes and MeOH (3 ml) was added. The resulting reaction mixture was stirred at reflux for 2 days. The crude reaction was washed with a 10% NH$_4$Cl solution and it was extracted with AcOEt. The organic layer was dried over Na$_2$SO$_4$, filtered and evaporated till dryness. The residue was purified first, in a manifold under vacuo with a sep-pak silica cartridge (5 g) (eluents=CH$_2$Cl$_2$ and CH$_2$Cl$_2$:MeOH (1,2%)), then, by HPLC with CH$_2$Cl$_2$:MeOH (2%) as eluent. Yield: 0.03 g of final compound 14 (29%).

Example B.15

Preparation of Final Compound 15

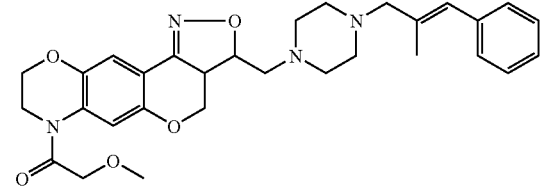

To a mixture of final compound 13 (prepared according to B 13) (0.00043 mol) and Et$_3$N (0.00065 mol) in CHCl$_3$ (4 ml), cooled with an ice-water bath, was added methoxyacetyl chloride (0.00043 mol) and the resulting reaction mixture was stirred at room temperature overnight. The crude reaction was washed with a saturated NaHCO$_3$ solution and it was extracted with CH$_2$Cl$_2$. The organic layer was dried over Na$_2$SO$_4$, filtered and evaporated till dryness. The residue was purified in a manifold under vacuo with a sep-pak silica cartridge (5 g) (eluents=CH$_2$Cl$_2$:acetone (10%) and CH$_2$Cl$_2$:MeOH (2%). Finally, the product crystallized with DIPE. Yield: 0.6782 g of final compound 15 (34%).

Example B.16

Preparation of Final Compound 16

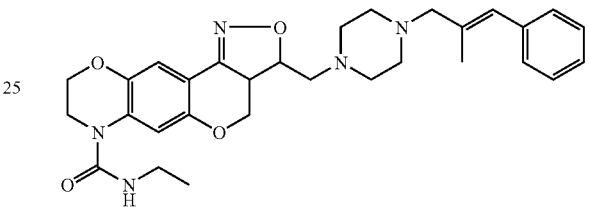

A mixture of final compound 13 (prepared according to B13) (0.00026 mol), EtNCO (0.00041 mol) and toluene (3 ml) was stirred at 75° C. overnight, in a sealed tube. The solvent was evaporated and the residu was purified in a manifold under vacuo with a sep-pak silica cartridge (5 g) (eluents=CH$_2$Cl$_2$, CH$_2$Cl$_2$:acetone 10% and CH$_2$Cl$_2$:MeOH 2%). Finally, the product as a syrup was crystallized from DIPE. Yield 0.0595 g of final compound 16 (43%).

In the following tables (Tables 1-4) a number of compounds are given which have been prepared according to any one of the Examples above. All compounds have also been tested for their pharmacological activity.

TABLE 1

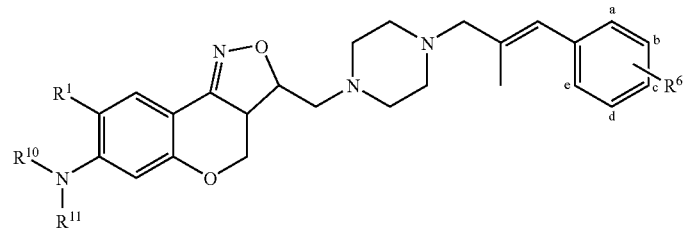

| Comp nr. | Ex. nr. | $R^1$ | $-R^{10}$ | $R^{11}$ | $R^6$ | Phys.data |
|---|---|---|---|---|---|---|
| 5 | B5 | H | H | H | — | [3α(E),3aα] |
| 8 | B8 | OCH$_3$ | H | H | — | [3α(E),3aα] |
| 86 | B8 | OCH$_3$ | H | H | b-F | [3α(E),3aα] |
| 87 | B5 | H | —CH$_3$ | H | — | [3α(E),3aα] HCl (1:2) |
| 88 | B11 | OCH$_3$ | —CH$_3$ | H | — | [3α(E),3aα] |
| 17 | B11 | OCH$_3$ | —CH$_3$ | H | b-F | [3α(E),3aα] |
| 18 | B1 | H | —CH$_2$CH$_3$ | H | — | [3α(E),3aα] |

TABLE 1-continued

| Comp nr. | Ex. nr. | $R^1$ | —$R^{10}$ | $R^{11}$ | $R^6$ | Phys.data |
|---|---|---|---|---|---|---|
| 105 | B9 | OCH₃ | —CH₂CH₃ | H | c-F | [3α(E),3aα] |
| 133 | B3 | H | n-pentyl | H | c-F | [3α(E),3aα] |
| 116 | B9 | OCH₃ | isobutyl | H | c-F | [3α(E),3aα] |
| 104 | B9 | OCH₃ | 2-methylbutyl | H | c-F | [3α(E),3aα] |
| 129 | B3 | H | isopropyl | H | c-F | [3α(E),3aα] |
| 131 | B3 | H | sec-butyl | H | c-F | [3α(E),3aα] |
| 99 | B9 | OCH₃ | sec-butyl | H | c-F | [3α(E),3aα] |
| 98 | B9 | OCH₃ | 1-methylbutyl | H | c-F | [3α(E),3aα] |
| 130 | B3 | H | cyclopropylmethyl | H | c-F | [3α(E),3aα] |
| 128 | B9 | OCH₃ | (1-methylcyclopropyl)methyl | H | c-F | [3α(E),3aα] |
| 126 | B9 | OCH₃ | cyclopropylethyl | H | c-F | [3α(E),3aα] |
| 19 | B1 | H | H₂N–CH₂CH₂– | CH₃ | c-F | [3α(E),3aα] HCl (1:1) |
| 97 | B9 | OCH₃ | H₂N–CH₂CH₂– | H | c-F | [3α(E),3aα] |
| 20 | B1 | H | CH₃NH–CH₂CH₂– | H | c-F | [3α(E),3aα] HCl (1:1) |
| 21 | B1 | H | CH₃NH–CH₂CH₂– | CH₃ | c-F | [3α(E),3aα] |

TABLE 1-continued

| Comp nr. | Ex. nr. | R[1] | —R[10] | R[11] | R[6] | Phys.data |
|---|---|---|---|---|---|---|
| 120 | B3 | H | (sec-pentyl)NH– | CH$_3$ | c-F | [3α(E),3aα] |
| 110 | B3 | H | (3-methylbut-2-yl)NH– | CH$_3$ | c-F | [3α(E),3aα] |
| 1 | B1 | H | (CH$_3$)$_2$N–CH$_2$– | CH$_3$ | — | [3α(E),3aα] HCl (1:2) |
| 22 | B1 | H | (CH$_3$)$_2$N–CH$_2$– | CH$_3$ | b-F | [3α(E),3aα] HCl (1:2) |
| 23 | B1 | H | (CH$_3$)$_2$N–CH$_2$– | CH$_3$ | c-F | [3α(E),3aα] HCl (1:1) |
| 9 | B9 | OCH$_3$ | (CH$_3$)$_2$N–CH$_2$– | H | — | [3α(E),3aα] |
| 24 | B9 | OCH$_3$ | (CH$_3$)$_2$N–CH$_2$– | H | c-F | [3α(E),3aα] |
| 11 | B11 | OCH$_3$ | (CH$_3$)$_2$N–CH$_2$– | CH$_3$ | — | [3α(E),3aα] |
| 25 | B1 | H | (C$_2$H$_5$)$_2$N–CH$_2$– | CH$_3$ | c-F | [3α(E),3aα] HCl (1:1) |
| 122 | B3 | H | (tert-butyl)(CH$_3$)N– | CH$_3$ | c-F | [3α(E),3aα] |
| 118 | B3 | H | cyclopropyl-CH$_2$–NH– | CH$_3$ | c-F | [3α(E),3aα] |
| 111 | B3 | H | cyclobutyl-NH– | CH$_3$ | c-F | [3α(E),3aα] |
| 119 | B3 | H | HO–CH(CH$_3$)–CH$_2$–NH– | CH$_3$ | c-F | [3α(E),3aα] |

TABLE 1-continued

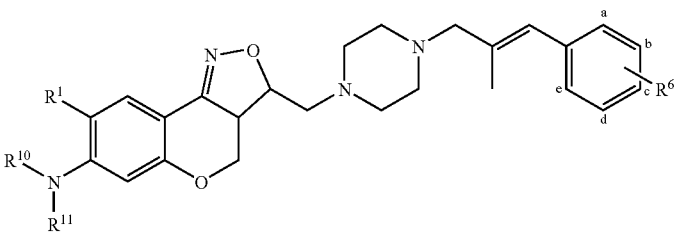

| Comp nr. | Ex. nr. | R¹ | —R¹⁰ | R¹¹ | R⁶ | Phys.data |
|---|---|---|---|---|---|---|
| 121 | B3 | H | allyl-N(CH₃)-propyl- | CH₃ | c-F | [3α(E),3aα] |
| 123 | B3 | H | azetidin-1-yl-propyl- | CH₃ | c-F | [3α(E),3aα] |
| 96 | B9 | OCH₃ | pyrrolidin-1-yl- | H | c-F | [3α(E),3aα] |
| 26 | B9 | OCH₃ | pyrrolidin-1-yl-propyl- | H | — | [3α(E),3aα] |
| 27 | B9 | OCH₃ | pyrrolidin-1-yl-propyl- | H | b-F | [3α(E),3aα] |
| 28 | B1 | H | pyrrolidin-1-yl-propyl- | H | c-F | [3α(E),3aα] |
| 29 | B9 | OCH₃ | pyrrolidin-1-yl-propyl- | H | c-F | [3α(E),3aα] |
| 30 | B1 | H | morpholin-4-yl-propyl- | H | c-F | [3α(E),3aα] |
| 31 | B1 | H | HO-ethyl- | CH₃ | — | [3α(E),3aα] |
| 32 | B9 | OCH₃ | HO-ethyl- | CH₃ | — | [3α(E),3aα] |
| 33 | B1 | H | HO-propyl- | CH₃ | — | A-[3α(E),3aα] |
| 34 | B1 | H | HO-propyl- | CH₃ | — | B-[3α(E),3aα] |
| 35 | B1 | H | HO-propyl- | CH₃ | b-F | [3α(E),3aα] |
| 36 | B9 | OCH₃ | HO-propyl- | CH₃ | b-F | [3α(E),3aα] |
| 37 | B1 | H | HO-propyl- | H | c-F | [3α(E),3aα] |
| 38 | B1 | H | HO-ethyl- | CH₃ | c-F | [3α(E),3aα] |

TABLE 1-continued

| Comp nr. | Ex. nr. | R¹ | —R¹⁰ | R¹¹ | R⁶ | Phys.data |
|---|---|---|---|---|---|---|
| 39 | B9 | OCH₃ | HO-CH₂-CH₂- | CH₃ | c-F | [3α(E),3aα] |
| 132 | B3 | H | HO-CH(CH₃)- | H | c-F | [3α(E),3aα] |
| 134 | B3 | H | HO-CH₂-CH(CH₃)- | H | c-F | [3α(E),3aα] |
| 117 | B3 | H | (CH₃)₃C-CH₂-C(O)O-CH₂-CH₂- | CH₃ | c-F | [3α(E),3aα] |
| 95 | B3 | H | CH₂=C(CH₃)-C(O)O-CH₂-CH₂- | CH₃ | c-F | [3α(E),3aα] |
| 109 | B3 | H | cyclopropyl-C(O)O-CH₂-CH₂- | CH₃ | c-F | [3α(E),3aα] |
| 108 | B3 | H | cyclobutyl-C(O)O-CH₂-CH₂- | CH₃ | c-F | [3α(E),3aα] |
| 127 | B3 | H | CH₃CH₂CH(CH₃)-NH-C(O)O-CH₂-CH₂- | CH₃ | c-F | [3α(E),3aα] |
| 40 | B2 | H | phenyl | H | — | [3α(E),3aα] |
| 41 | B2 | H | phenyl | CH₃ | — | [3α(E),3aα] |
| 42 | B2 | H | 4-fluorophenyl | H | — | [3α(E),3aα] |

TABLE 1-continued

| Comp nr. | Ex. nr. | $R^1$ | —$R^{10}$ | $R^{11}$ | $R^6$ | Phys.data |
|---|---|---|---|---|---|---|
| 43 | B2 | H | 4-methoxyphenyl | H | c-F | [3α(E),3aα] |
| 44 | B2 | H | 3-cyanophenyl | H | — | [3α(E),3aα] |
| 45 | B2 | H | 2-methylphenyl | H | — | [3α(E),3aα] |
| 46 | B2 | H | 3,4-dimethylphenyl | H | — | [3α(E),3aα] |
| 47 | B1 | H | benzyl | $CH_3$ | — | [3α(E),3aα] |
| 48 | B1 | H | benzyl | $CH_3$ | — | [3α(E),3aα] HCl (1:2) |
| 2 | B1 | H | benzyl | H | — | [3α(E),3aα] |
| 100 | B9 | $OCH_3$ | pyridin-4-yl | H | c-F | [3α(E),3aα] |
| 6 | B6 | H | acetyl | H | — | [3α(E),3aα] |
| 10 | B10 | $OCH_3$ | acetyl | H | — | [3α(E),3aα] |
| 49 | B10 | $OCH_3$ | acetyl | H | b-F | [3α(E),3aα] |
| 113 | B10 | $OCH_3$ | 2-methylpentanoyl | H | c-F | [3α(E),3aα] |

TABLE 1-continued

| Comp nr. | Ex. nr. | $R^1$ | $-R^{10}$ | $R^{11}$ | $R^6$ | Phys.data |
|---|---|---|---|---|---|---|
| 114 | B10 | OCH$_3$ | 2-methylbutanoyl | H | c-F | [3α(E),3aα] |
| 50 | B6 | H | pivaloyl (tert-butyl C(=O)-) | H | — | [3α(E),3aα] |
| 51 | B6 | H | cyclopropylcarbonyl | H | — | [3α(E),3aα] |
| 138 | B3 | H | cyclopropylcarbonyl | H | c-F | [3α(E),3aα] |
| 52 | B10 | OCH$_3$ | cyclopropylcarbonyl | H | — | [3α(E),3aα] |
| 53 | B10 | OCH$_3$ | cyclopropylcarbonyl | H | b-F | [3α(E),3aα] |
| 115 | B10 | OCH$_3$ | cyclobutylcarbonyl | H | c-F | [3α(E),3aα] |
| 54 | B6 | H | acryloyl (CH$_2$=CH-C(=O)-) | H | — | [3α(E),3aα] |
| 106 | B10 | OCH$_3$ | acryloyl | H | c-F | [3α(E),3aα] |
| 112 | B10 | OCH$_3$ | crotonoyl (CH$_3$-CH=CH-C(=O)-) | H | c-F | [3α(E),3aα] |

TABLE 1-continued

| Comp nr. | Ex. nr. | R¹ | —R¹⁰ | R¹¹ | R⁶ | Phys.data |
|---|---|---|---|---|---|---|
| 55 | B6 | H | benzoyl (C(=O)Ph) | H | — | [3α(E),3aα] |
| 56 | B6 | H | pyrrolidine-2-carbonyl | H | — | [3α(E),3aα, 7(R)] |
| 57 | B6 | H | pyrrolidine-2-carbonyl | H | — | [3α(E),3aα, 7(S)] |
| 58 | B6 | H | tert-butoxycarbonyl (Boc) | H | c-F | [3α(E),3aα] |
| 137 | B7 | H | H₂N-C(=O)- | H | c-F | [3α(E),3aα] |
| 59 | B7 | H | ethylaminocarbonyl | H | — | [3α(E),3aα] |
| 60 | B7 | H | ethylaminocarbonyl | ethylaminocarbonyl | c-F | [3α(E),3aα] |
| 61 | B7 | H | tert-butylaminocarbonyl | H | — | [3α(E),3aα] |
| 62 | B7 | H | cyclohexylaminocarbonyl | H | — | [3α(E),3aα] |
| 63 | B7 | H | ethoxycarbonylmethylaminocarbonyl | H | — | [3α(E),3aα] |

TABLE 1-continued
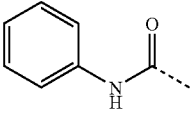
| Comp nr. | Ex. nr. | R¹ | —R¹⁰ | R¹¹ | R⁶ | Phys.data |
|---|---|---|---|---|---|---|
| 64 | B7 | H | 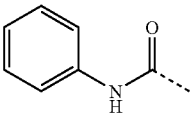 | H | — | [3α(E),3aα] |
| 124 | B10 | OCH₃ | 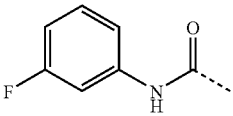 | H | c-F | [3α(E),3aα] |
| 65 | B7 | H | 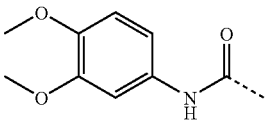 | H | — | [3α(E),3aα] |
| 7 | B7 | H | 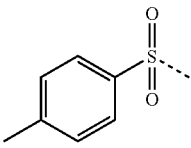 | H | — | [3α(E),3aα] |
| 66 | B6 | H | —SO₂CH₃ | —SO₂CH₃ | — | [3α(E),3aα] |
| 3 | B3 | H | 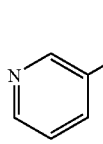 | H | c-F | [3α(E),3aα] |
| 67 | B6 | H | 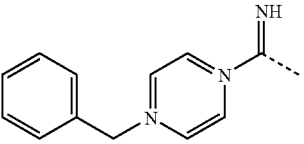 | H | — | [3α(E),3aα] |
| 68 | B7 | H |  | H | c-F | [3α(E),3aα] |

TABLE 2
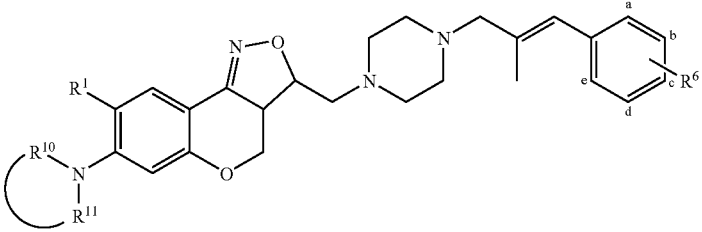
| Comp nr. | Ex. nr. | $R^1$ | $R^{10}$-N-$R^{11}$ | $R^6$ | Phys.data |
|---|---|---|---|---|---|
| 102 | B9 | OCH$_3$ | 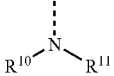 | c-F | [3α(E), 3aα] |
| 107 | B9 | OCH$_3$ | 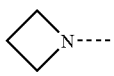 | c-F | [3α(E), 3aα] |
| 69 | B1 | H | 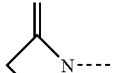 | c-F | [3α(E), 3aα] |
| 70 | B1 | H | 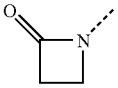 | c-F | [3α(E), 3aα] |
| 101 | B9 | OCH$_3$ | 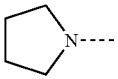 | c-F | [3α(E), 3aα] |
| 139 | B3 | H | 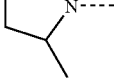 | c-F | [3α(E), 3aα] |
| 71 | B1 | H | 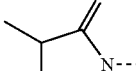 | c-F | [3α(E), 3aα] |
| 135 | B3 | H | 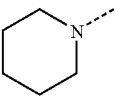 | c-F | [3α(E), 3aα] |
| 103 | B9 | OCH$_3$ |  | c-F | [3α(E), 3aα] |
| 72 | B1 | H | 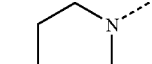 | c-F | [3α(E), 3aα] |

TABLE 2-continued
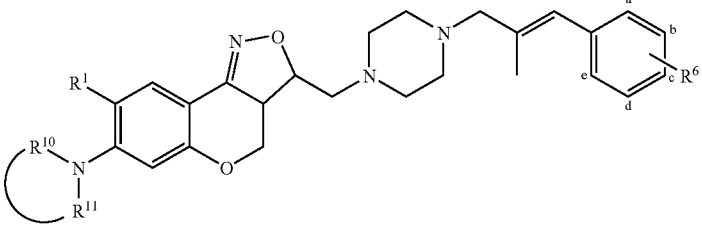
| Comp nr. | Ex. nr. | R¹ | 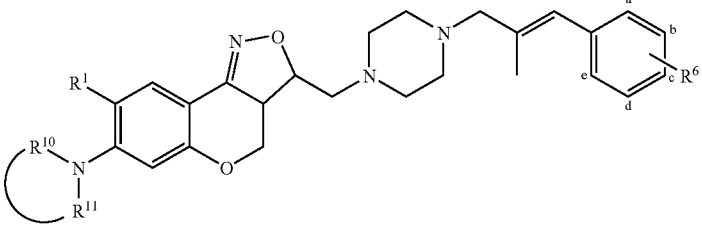 | R⁶ | Phys.data |
|---|---|---|---|---|---|
| 73 | B1 | H | 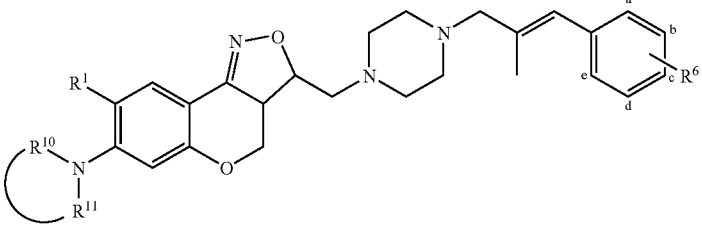 | c-F | [3α(E), 3aα] |
| 125 | B1 | H | 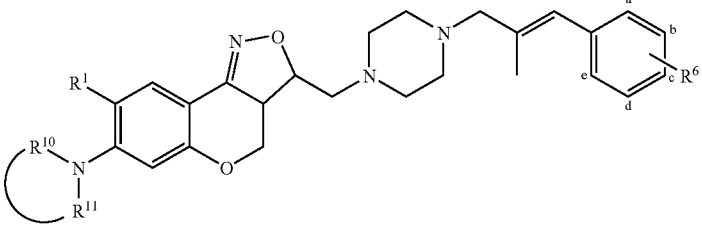 | c-F | [3α(E), 3aα] |
| 136 | B3 | H | 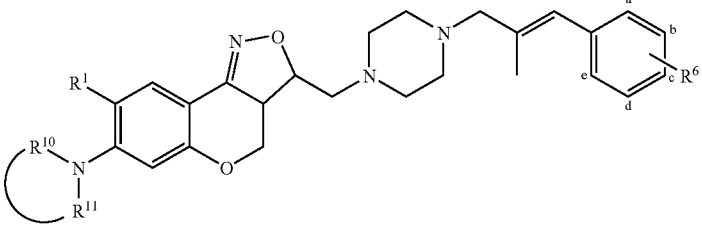 | c-F | [3α(E), 3aα] |
| 75 | B9 | OCH₃ | 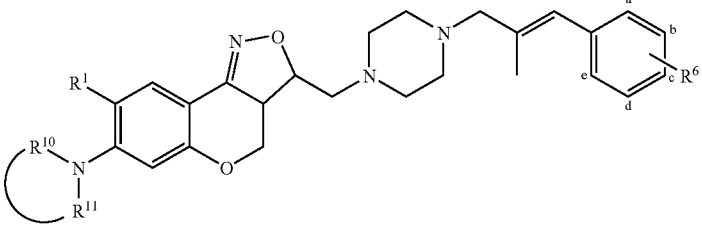 | — | [3α(E), 3aα] |
| 76 | B9 | OCH₃ | 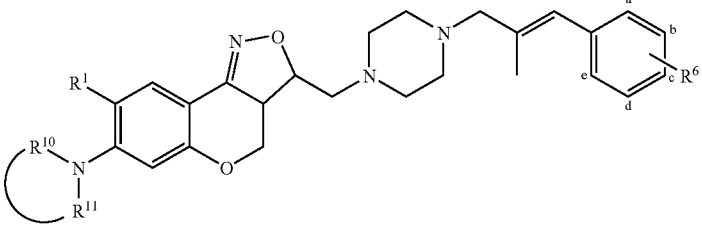 | b-F | [3α(E), 3aα] |
| 77 | B1 | H | 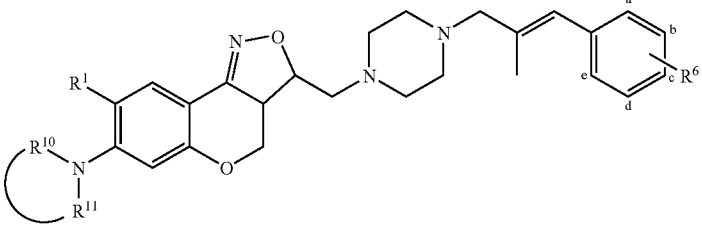 | c-F | [3α(E), 3aα] |
| 78 | B9 | OCH₃ | 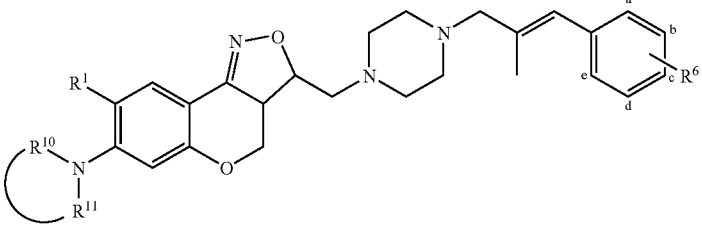 | c-F | [3α(E), 3aα] |
| 79 | B1 | H | 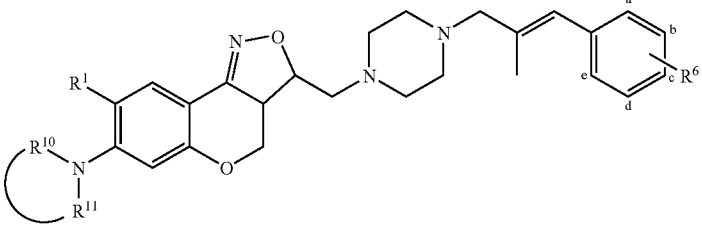 | c-F | [3α(E), 3aα] |
| 80 | B1 | H | 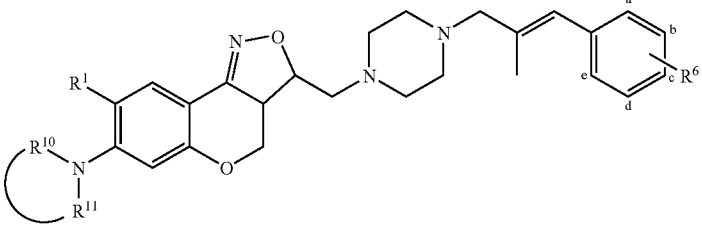 | c-F | [3α(E), 3aα] |
| 81 | B3 | H | 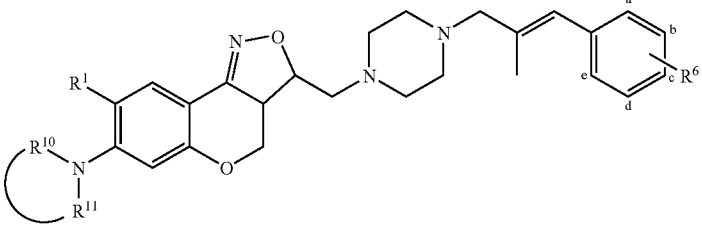 | c-F | [3α(E), 3aα, 7(E)] |
| 82 | B9 | OCH₃ | 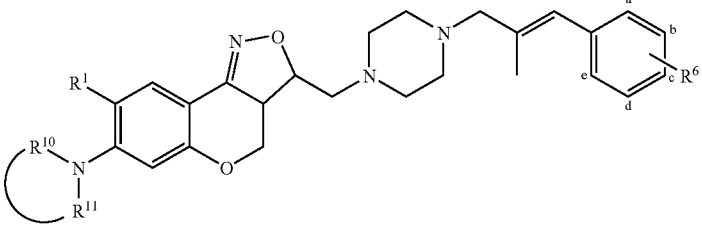 | — | [3α(E), 3aα] |

TABLE 2-continued

| Comp nr. | Ex. nr. | R¹ | R¹⁰-N-R¹¹ | R⁶ | Phys.data |
|---|---|---|---|---|---|
| 83 | B9 | OCH₃ | morpholinyl | b-F | [3α(E), 3aα] |
| 84 | B1 | H | morpholinyl | c-F | [3α(E), 3aα] |
| 85 | B9 | OCH₃ | morpholinyl | c-F | [3α(E), 3aα] |

TABLE 3

| Comp nr. | Ex. nr. | R¹⁴ | R³ | Phys.data |
|---|---|---|---|---|
| 13 | B12 | H | CH₂C(CH₃)=CH-phenyl | [3α(E), 3aα] |
| 89 | B12 | H | CH₂C(CH₃)=CH-(3-F-phenyl) | [3α(E), 3aα] |
| 90 | B12 | H | CH₂C(CH₃)=CH-(4-F-phenyl) | [3α(E), 3aα] |
| 91 | B12 | H | CH₂CH=C(CH₃)-phenyl | [3α(E), 3aα] |

TABLE 3-continued

| Comp nr. | Ex. nr. | R14 | R3 | Phys.data |
|---|---|---|---|---|
| 92 | B12 | H | 2-naphthylmethyl | [3α(E), 3aα] |
| 14 | B14 | CH3 | β-methylcinnamyl | [3α(E), 3aα] |
| 12 | A3 | acetyl | β-methylcinnamyl | [3α(E), 3aα] |
| 15 | B15 | methoxyacetyl | β-methylcinnamyl | [3α(E), 3aα] |
| 16 | B16 | ethylaminocarbonyl | β-methylcinnamyl | [3α(E), 3aα] |
| 94 | B12 | H | 4-chlorobenzyl | [3α(E), 3aα] |

TABLE 4

| Comp nr. | Ex. nr. | —R1 | R2 | R4 | d | Z | Phys.data-configuration |
|---|---|---|---|---|---|---|---|
| 4 | B4 | morpholin-4-yl | H | H | double bond | =CH— | [3α(E), 3aα] |
| 93 | B4 | 4-methoxyphenylamino | H | H | double bond | =CH— | [3α(E), 3aα] |

TABLE 4-continued

| Comp nr. | Ex. nr. | —R¹ | R² | R⁴ | d | Z | Phys.data-configuration |
|---|---|---|---|---|---|---|---|
| 140 | B4 | OCH₃ | (CH₃)N-CH₂CH₂-N(CH₃)- | | | cyclopropyl | [3α(E), 3aα] |

For a selection of 50 compounds, melting points were obtained with a Bücchi melting point apparatus B-545. The heating medium is a metal block. The melting of the sample is visually observed by a magnifying lense and a big light contrast. Melting points are measured with a temperature gradient of 3 degrees Celsius/minute. The results are summarized in Table 5.

TABLE 5

Melting points

| Co. No. | Melting point (° C.) | Visual observation |
|---|---|---|
| 2 | 108.9-114.7 | light yellow liquid |
| 3 | 177.0-194.1 | At 177° C. yellow sticky product, at 194.1° C. brown liquid |
| 4 | 121.8-125.9 | At 123° C. light yellow sticky product, at 125.9° C. light brown liquid |
| 5 | 134.1-136.2 | At 130° C. changing to light brown crystals, at 136° C. brown liquid |
| 6 | 112.1-126.7 | At 117° C. sticky product, at 126.7° C. sticky light brown liquid |
| 7 | 202.2-207.1 | At 202.2°0 C. shrinking, brown liquid at 207.1° C. |
| 9 | 154.5-157.9 | At 157.9° C. brown liquid |
| 13 | 120.0-145.4 | At 120° C. shrinking to light brown crystals, 140° C. sticky crystals, at 145.4° C. brown sticky liquid |
| 15 | 118.9-127.6 | At 119° C. shrinking, at 123° C. light brown sticky product, at 127° C. sticky light brown liquid |
| 19 | 218-about 226 | At 218° C. changing to dark brown crystals, shrinking at 226° C. black sticky, no exact end to see. |
| 20 | 199.0-about 235.5 | At 199° C. crystals changing to dark grey, at 218° C. black sticky crystals, at 235.5° C. black sticky liquid foam, exact end difficult to see. |
| 21 | 98.4-105.3 | At 98.4° C. shrinking, at 105.3° C. light brown sticky liquid |
| 24 | 157.7-159.9 | At 157.7° C. shrinking, at 159.9° C. dark brown liquid. |
| 26 | 120.4-123.0 | At 120° C. shrinking, at 123° C. sticky light yellow liquid |
| 28 | 108.3-121.8 | At 108.3° C. shrinking, at 121.8° C. light yellow liquid |
| 30 | 123.0-about 229 | At 123° C. shrinking, changing colour to light brown, at 129° C. totally sticky; exact end difficult to see |
| 33 | 114.3-117.2 | light yellow liquid |
| 34 | 190.0-about 200 | At 190° C. shrinking, sticky crystals in capillary, decomposition at 200° C. |
| 37 | 129.0-135.4 | At 129° C. sticky product, at 135.4° C. light brown liquid |
| 38 | 167.5-172.6 | At 167.5° C. shrinking, at 172.6° C. brown sticky liquid |
| 40 | 127.1-131.4 | At 127° C. shrinking, at 131.4° C. light yellow liquid |
| 41 | 125.9-139.7 | At 126° C. sticky brown product, at 139.7° C. brown liquid |
| 42 | 130.8-134.1 | At 130.8° C. shrinking, at 132° C. sticky liquid, at 134° C. light brown product |
| 43 | 131.7-134.5 | Dark brown liquid |
| 44 | 152.7-162.6 | At 156° C. sticky product, at 162.6° C. brown liquid |
| 45 | 133.3-148.9 | At 136° C. sticky product, at 148.9° C. light yellow liquid |
| 46 | 138.9-151.3 | Changing to light brown liquid, at 138.9° C. sticky crystals, at 151.3° C. brown liquid |
| 50 | 183.4-190.2 | At 188.1° C. sticky product, at 190.2° C. sticky brown liquid |
| 54 | 136.1-172.9 | At 136.1° C. shrinking and changing slowly to light brown crystals, at 155° C. sticky product |
| 61 | 98.4-113.5 | At 98.4° C. sticky light brown crystals, at 113.5° C. sticky brown liquid |
| 62 | 121.1-about 136.5 | At 118° C. changing to light brown product, at 121.1° C. sticky product, at 136.5° C. bubbles of crystals in liquid, exact end difficult to see |
| 63 | 175.3-about 177 | At 160° C. colour crystals changing to brown, at 175° C. shrinking crystals, at 177° C. sticky liquid with bubbles or crystals at the wall, exact end difficult to see |

TABLE 5-continued

Melting points

| Co. No. | Melting point (° C.) | Visual observation |
|---|---|---|
| 64 | 180.3-181.6 | At 177° C. changing to light brown crystals, at 181.6° C. sticky liquid product |
| 65 | 186.8-188.5 | At 188.5° C. light brown liquid |
| 66 | 201.8-202.9 | At 198° C. light brown product, at 201.8° C. sticky product, at 202.9° C. brown liquid |
| 70 | 194.7-204.9 | At 194.7° C. shrinking, at 200° C. sticky brown product, at 204.9° C. brown liquid |
| 71 | 168.2-169.4 | At 163° C. changing to light brown colour, at 169.4° C. sticky liquid |
| 72 | 156.4-161.0 | At 156.5° C. sticky product, at 161° C. sticky brown liquid |
| 75 | 142.8-144.4 | At 142.8° C. shrinking and changing to light brown, at 144.4° C. light brown liquid |
| 77 | 147.3-150.6 | At 150.6° C. light brown liquid |
| 79 | 203.5-206.2 | At 206.2° C. dark brown liquid |
| 80 | 166.4-178.2 | At 168° C. shrinking, at 173 ° C. sticky product, at 174.3° C. brown liquid |
| 81 | 154.9-160.4 | At 154.9° C. shrinking, at 160.0° C. brown sticky liquid |
| 82 | 143.5-145.9 | At 145.9° C. brown liquid |
| 84 | 179.2-188.8 | At 179° C. shrinking, at 185° C. sticky product, at 188.8° C. brown liquid |
| 89 | 145.4-153.1 | Before 145 ° C. changing colour to light brown, at 145.4° C. sticky product and shrinking, at 153.1° C. sticky brown liquid |
| 90 | 160.6-172.2 | At 160.6° C. shrinking brown sticky product, at 172.1° C. brown liquid |
| 91 | 130.4-about 146.4 | At 130.4° C. shrinking, at 146.4° C. sticky brown liquid product, exact end difficult to see |
| 92 | 85.3-103.9 | At 85.3° C. shrinking, at 103.7° C. sticky liquid product light brown |
| 94 | 186.5-about 198 | At 186.5° C. slowly shrinking and changing colour to brown, at 196° C. brown black sticky liquid, at 198° C. black dark brown liquid. |

C. Pharmacological Examples

Example C1

Binding Experiment for $\alpha_2$-Adrenergic Receptor Subtypes and for 5-HT Transporter General The interaction of the compounds of Formula (I) with h$\alpha_2$-receptors and h5-HT-transporters was assessed in in vitro radioligand binding experiments. In general, a low concentration of a radioligand with a high binding affinity for a particular receptor or transporter is incubated with a sample of a tissue preparation enriched in a particular receptor or transporter or with a preparation of cells expressing cloned human receptors in a buffered medium. During the incubation, the radioligand binds to the receptor or transporter. When equilibrium of binding is reached, the receptor bound radioactivity is separated from the non-bound radioactivity, and the receptor- or transporter-bound activity is counted. The interaction of the test compounds with the receptor is assessed in competition binding experiments. Various concentrations of the test compound are added to the incubation mixture containing the receptor- or transporter preparation and the radioligand. The test compound in proportion to its binding affinity and its concentration inhibits binding of the radioligand. The radioligand used for h$\alpha_{2A}$, h$\alpha_{2B}$ and h$\alpha_{2C}$ receptor binding was [$^3$H]raulwolscine and for the h5-HT transporter was [$^3$H]paroxetine.

Cell Culture and Membrane Preparation.

CHO cells, stabile transfected with human adrenergic-$\alpha_{2A}$-, -$\alpha_{2B}$ or $\alpha_{2C}$ receptor cDNA, were cultured in Dulbecco's Modified Eagle's Medium (DMEM)/Nutrient mixture Ham's F12 (ratio 1:1)(Gibco, Gent-Belgium) supplemented with 10% heat inactivated fetal calf serum (Life Technologies, Merelbeke-Belgium) and antibiotics (100 IU/ml penicillin G, 100 µg/ml streptomycin sulphate, 110 µg/ml pyruvic acid and 100 µg/ml L-glutamine). One day before collection, cells were induced with 5 mM sodiumbutyrate. Upon 80-90% of confluence, cells were scraped in phosphate buffered saline without $Ca^{2+}$ and $Mg^{2+}$ and collected by centrifugation at 1500×g for 10 min. The cells were homogenised in Tris-HCl 50 mM using an Ultraturrax homogenizer and centrifuged for 10 min at 23,500×g. The pellet was washed once by resuspension and rehomogenization and the final pellet was resuspended in Tris-HCl, divided in 1 ml aliquots and stored at −70° C.

Binding Experiment for $\alpha_2$-Adrenergic Receptor Subtypes

Membranes were thawed and re-homogenized in incubation buffer (glycylglycine 25 mM, pH 8.0). In a total volume of 500 µl, 2-10 µg protein was incubated with [$^3$H]raulwolscine (NET-722) (New England Nuclear, USA) (1 nM final concentration) with or without competitor for 60 min at 25° C. followed by rapid filtration over GF/B filter using a Filtermatel 96 harvester (Packard, Meriden, Conn.). Filters were rinsed extensively with ice-cold rinsing buffer (Tris-HCl 50 mM pH 7.4). Filter-bound radioactivity was determined by scintillation counting in a Topcount (Packard, Meriden, Conn.) and results were expressed as counts per minute (cpm). Non-specific binding was determined in the presence of 1 µM oxymetazoline for h$\alpha_{2A}$- and h$\alpha_{2B}$ receptors and 1 µM spiroxatrine for h$\alpha_{2C}$ receptors.

Binding Experiment for 5-HT Transporter

Human platelet membranes (Oceanix Biosciences Corporation, Hanover, Md., USA) were thawed, diluted in buffer (Tris-HCl 50 mM, 120 mM NaCl and 5 mM KCl) and quickly (max 3 s) homogenised with an Ultraturrax homogenizer. In a total volume of 250 µL, 50-100 µg protein was incubated with [$^3$H]paroxetine (NET-869) (New England Nuclear, USA) (0.5 nM final concentration) with or without competitor for 60 min at 25° C. Incubation was stopped by rapid filtration of the incubation mixture over GF/B filters, pre-wetted with 0.1% polyethyleneamine, using a Filtermatel 96 harvester (Packard, Meriden, Conn.). Filters were rinsed extensively with ice-cold buffer and radioactivity on the filters was counted in a Topcount liquid scintillation counter (Packard, Meriden, Conn.). Data were expressed as cpm. Imipramine (at 1 μM final concentration) was used to determine the non-specific binding.

Data Analysis and Results

Data from assays in the presence of compound were calculated as a percentage of total binding measured in the absence of test compound. Inhibition curves, plotting percent of total binding versus the log value of the concentration of the test compound, were automatically generated, and sigmoidal inhibition curves were fitted using non-linear regression. The $pIC_{50}$ values of test compounds were derived from individual curves.

All compounds according to formula (I) produced an inhibition at least at the $h\alpha_{2A}$ site (but often also at the $h\alpha_{2B}$ and $h\alpha_{2C}$ sites) and simultaneously at the 5-HT transporter site of more than 50% ($pIC_{50}$) at a test concentration ranging between $10^{-6}$ M and $10^{-9}$ M in a concentration-dependent manner. Results are shown in Table 6.

TABLE 6

$pIC_{50}$-values for the $h\alpha_{2A}$, $h\alpha_{2c}$ and 5-HT transporter receptor site.

| Co nr. | $\alpha_{2A}$ | $\alpha_{2C}$ | HTT |
|---|---|---|---|
| 49 | 8.9 | 9.6 | 8.1 |
| 1 | 8.9 | 9 | 8.2 |
| 31 | 8.9 | 8.9 | 7.6 |
| 54 | 8.8 | 9.1 | 7.6 |
| 75 | 8.8 | >9 | 8.1 |
| 51 | 8.8 | 9.0 | 7.8 |
| 22 | 8.8 | 8.9 | 8.8 |
| 82 | 8.8 | 8.9 | 7.4 |
| 34 | 8.7 | 9.4 | 7.2 |
| 12 | 8.7 | 9.0 | 7.5 |
| 67 | 8.7 | 8.9 | 7.9 |
| 11 | 8.7 | 8.8 | 8.5 |
| 47 | 8.6 | 8.5 | 7.3 |
| 87 | 8.6 | 8.5 | 7.3 |
| 5 | 8.6 | 8.4 | 7.0 |
| 56 | 8.5 | 9.3 | 7.9 |
| 15 | 8.5 | 9.1 | 8.0 |
| 50 | 8.5 | 9.0 | 7.8 |
| 35 | 8.5 | 8.9 | 8.1 |
| 69 | 8.5 | 8.9 | 7.7 |
| 6 | 8.5 | 8.6 | 7.3 |
| 37 | 8.5 | 8.3 | 7.2 |
| 53 | 8.4 | 9.2 | 8.0 |
| 13 | 8.4 | 9.2 | 7.9 |
| 52 | 8.4 | 9.2 | 7.7 |
| 76 | 8.4 | 9.1 | 8.5 |
| 32 | 8.4 | 9.1 | 7.7 |
| 89 | 8.4 | 9.0 | 8.4 |
| 10 | 8.4 | 8.9 | 7.2 |
| 66 | 8.3 | 9.3 | 7.4 |
| 57 | 8.3 | 9.2 | 7.6 |
| 26 | 8.3 | >9 | 8.5 |
| 88 | 8.3 | 8.9 | 7.7 |
| 8 | 8.3 | 8.8 | 7.6 |
| 55 | 8.3 | 8.5 | 7.6 |
| 9 | 8.3 | 6.0 | 8.3 |
| 25 | 8.2 | 9.4 | 8.1 |
| 84 | 8.2 | 8.9 | 7.6 |
| 18 | 8.2 | 8.9 | 7.3 |
| 86 | 8.2 | 8.8 | 8.3 |
| 137 | 8.2 | 8.0 | 7.7 |
| 91 | 8.2 | 8.8 | 7.5 |
| 106 | 8.2 | 7.9 | 7.5 |
| 16 | 8.1 | 9.1 | 8.1 |
| 59 | 8.1 | 8.9 | 8.0 |

TABLE 6-continued $pIC_{50}$-values for the $h\alpha_{2A}$, $h\alpha_{2c}$ and 5-HT transporter receptor site.

| Co nr. | $\alpha_{2A}$ | $\alpha_{2C}$ | HTT |
|---|---|---|---|
| 63 | 8.1 | 8.8 | 7.5 |
| 21 | 8.1 | 8.7 | 8.4 |
| 17 | 8.1 | 8.7 | 7.9 |
| 61 | 8.1 | 8.7 | 7.7 |
| 83 | 8.1 | 8.6 | 7.8 |
| 107 | 8.1 | 8.0 | 7.3 |
| 23 | 8.0 | 8.7 | 8.3 |
| 123 | 8.0 | 8.5 | 8.1 |
| 119 | 8.0 | 8.5 | 8.5 |
| 85 | 8.0 | 8.5 | 7.2 |
| 100 | 8.0 | 8.3 | 8.0 |
| 19 | 7.9 | 8.6 | 8.0 |
| 4 | 7.9 | 8.6 | <6 |
| 118 | 7.9 | 8.5 | 8.5 |
| 70 | 7.9 | 8.1 | 7.0 |
| 29 | 7.8 | 8.8 | 8.5 |
| 90 | 7.8 | 8.8 | 7.8 |
| 27 | 7.8 | 8.5 | 8.3 |
| 7 | 7.8 | 8.3 | 7.5 |
| 14 | 7.8 | 8.3 | 7.5 |
| 139 | 7.8 | 8.1 | 6.9 |
| 40 | 7.8 | 8.0 | 7.3 |
| 44 | 7.8 | 7.7 | 7.8 |
| 2 | 7.8 | .1 | 7.5 |
| 92 | 7.7 | 8.6 | 8.3 |
| 36 | 7.7 | 8.6 | 7.6 |
| 45 | 7.7 | 7.7 | 7.1 |
| 102 | 7.7 | 7.8 | 7.3 |
| 93 | 7.7 | 7.2 | 6.4 |
| 24 | 7.6 | 8.8 | 8.3 |
| 111 | 7.6 | 8.2 | 7.9 |
| 62 | 7.6 | 8.2 | 7.4 |
| 132 | 7.6 | 7.5 | 7.2 |
| 64 | 7.6 | 7.8 | 6.6 |
| 41 | 7.6 | 7.6 | 6.8 |
| 114 | 7.6 | 7.7 | 7.5 |
| 20 | 7.5 | 8.5 | 8.1 |
| 138 | 7.5 | 7.5 | 7.3 |
| 42 | 7.5 | 7.8 | 6.9 |
| 97 | 7.5 | 8.2 | 7.8 |
| 136 | 7.4 | 8.3 | 8.1 |
| 77 | 7.4 | 8.6 | 8.5 |
| 110 | 7.4 | 8.3 | 8.3 |
| 122 | 7.4 | 8.1 | 8.2 |
| 120 | 7.4 | 8.2 | 8.6 |
| 135 | 7.4 | 7.6 | 7.1 |
| 68 | 7.4 | 7.7 | 7.8 |
| 48 | 7.4 | 7.5 | 6.8 |
| 101 | 7.4 | 7.5 | 6.8 |
| 115 | 7.4 | 7.4 | 7.6 |
| 30 | 7.3 | 8.4 | 8.0 |
| 73 | 7.3 | 8.3 | 7.2 |
| 39 | 7.3 | 8.0 | 7.1 |
| 105 | 7.3 | 7.5 | 7.7 |
| 99 | 7.3 | 7.3 | 6.8 |
| 28 | 7.2 | 8.4 | 8.5 |
| 134 | 7.2 | 6.9 | 6.9 |
| 71 | 7.2 | 8.2 | 7.0 |
| 129 | 7.2 | 7.5 | 6.8 |
| 58 | 7.2 | 7.5 | 7.5 |
| 46 | 7.2 | 7.4 | 6.5 |
| 126 | 7.2 | 6.9 | 6.9 |
| 38 | 7.1 | 8.8 | 7.9 |
| 3 | 7.1 | 7.5 | 7.4 |
| 65 | 7.1 | 7.5 | 5.8 |
| 103 | 7.1 | 7.2 | 6.9 |
| 113 | 7.1 | 7.4 | 7.2 |
| 72 | 7.0 | 7.7 | 6.2 |
| 80 | 6.9 | 8.4 | 6.9 |
| 81 | 6.9 | 7.7 | 7.2 |
| 130 | 6.9 | 7.6 | 6.9 |
| 133 | 6.9 | 6.9 | 6.9 |

TABLE 6-continued pIC$_{50}$-values for the hα$_{2A}$, hα$_{2c}$ and 5-HT transporter receptor site.

| Co nr. | pIC$_{50}$ | | |
|---|---|---|---|
| | α$_{2A}$ | α$_{2C}$ | HTT |
| 96 | 6.9 | 6.9 | 6.7 |
| 98 | 6.9 | 7.0 | 6.6 |
| 104 | 6.9 | 6.9 | 6.5 |
| 109 | 6.8 | 7.5 | 7.4 |
| 131 | 6.8 | 7.3 | 7.2 |
| 108 | 6.7 | 7.3 | 7.1 |
| 125 | 6.7 | 6.8 | 6.8 |
| 116 | 6.7 | 6.8 | 7.1 |
| 128 | 6.7 | 6.7 | 6.8 |
| 79 | 6.6 | 8.1 | 6.7 |
| 117 | 6.6 | 6.9 | 7.0 |
| 94 | 6.5 | 7.5 | 6.9 |
| 127 | 6.5 | 6.8 | 6.7 |
| 124 | 6.5 | 6.8 | 7.3 |
| 43 | 6.4 | 6.9 | 6.2 |
| 121 | 6.3 | 7.0 | 6.8 |
| 33 | 6.2 | 7.4 | 7.9 |
| 60 | 5.5 | 6.4 | 5.2 |

The invention claimed is:

1. A compound according to the general Formula (I)

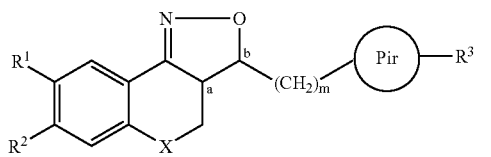

(I)

the pharmaceutically acceptable acid or base addition salts thereof, the stereochemically isomeric forms thereof and the N-oxide form thereof, wherein:

X is CH$_2$, N—R$^7$, S or O;

R$^7$ is selected from the group of hydrogen, alkyl, Ar, Ar-alkyl, alkylcarbonyl, alkyloxycarbonyl and mono- and di(alkyl)aminocarbonyl;

R$^1$ and R$^2$ are each selected from the group of hydrogen, hydroxy, cyano, halo, OSO$_2$H, OSO$_2$CH$_3$, N—R$^{10}$R$^{11}$, alkyloxy, alkyloxyalkyloxy, alkyloxyalkyloxyalkyloxy, tetrahydrofuranyloxy, alkylthio, alkylcarbonyloxy, alkyloxyalkylcarbonyloxy, pyridinylcarbonyloxy, alkylcarbonyloxyalkyloxy, alkyloxycarbonyloxy, alkenyloxy, alkenylcarbonyloxy and mono- or di(alkyl)aminoalkyloxy;

with the proviso that at least one of R$^1$ and R$^2$ is N—R$^{10}$R$^{11}$ wherein:

R$^{10}$ and R$^{11}$ are each, independently from each other, selected from the group of hydrogen, alkyl, Het, Ar, Ar-alkyl, Het- alkyl, mono- or di(alkyl)aminoalkyl, mono- or di(alkenyl)aminoalkyl, alkylcarbonyl, alkenylcarbonyl, Ar-carbonyl, Het-carbonyl, alkyloxycarbonyl, aminocarbonyl, mono- or di(alkyl)aminocarbonyl, mono- or di(Ar)aminocarbonyl, mono- or di(alkyloxycarbonylalkyl)aminocarbonyl, alkylcarbonyloxyalkyl, alkenylcarbonyloxyalkyl, mono- or di(alkyl)aminocarbonyloxyalkyl, aminoiminomethyl, alkylaminoiminomethyl, N-benzylpiperazinyliminomethyl, alkylsulphonyl and Ar-sulphonyl ; or R$^{10}$ R$^{11}$ may be taken together and with the N may form a monovalent radical selected from the group of

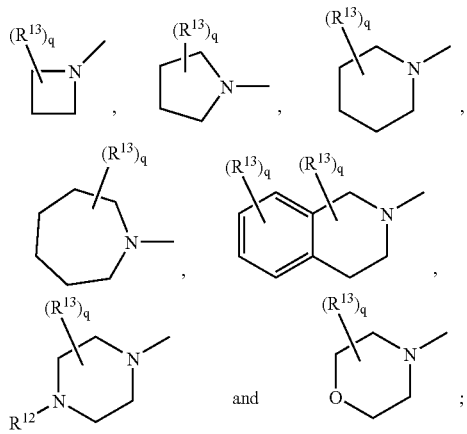

wherein:

R$^{12}$ selected from the group of hydrogen, alkyl, Ar, Ar-alkyl, Ar-alkenyl, alkylcarbonyl, alkyloxycarbonyl, alkyloxyalkylcarbonyl and mono- or di(alkyl)-aminocarbonyl;

each ring having optionally 1, 2 or 3 double bonds and each ring being optionally substituted with q radicals R$^{13}$, each radical R$^{13}$ independently from each other selected from the group of alkyl, oxo, Ar, Ar-alkyl, Ar-alkenyl and alkyloxycarbonyl and q being an integer ranging from 0 to 6;

a and b are asymmetric centers;

(CH$_2$)$_m$ is a straight hydrocarbon chain of m carbon atoms, m being an integer ranging from 1 to 4;

Pir is a radical according to any one of Formula (IIa), (IIb) or (IIc)

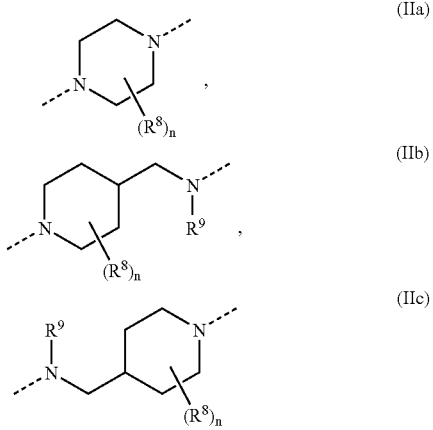

optionally substituted with n radicals R$^8$, wherein:

each R$^8$ is independently from each other, selected from the group of hydroxy, amino, nitro, cyano, halo and alkyl;

n is an integer ranging from 0 to 5;

R$^9$ is selected from the group of hydrogen, alkyl and formyl;

R³ is a radical according to any one of Formula (IIIa), (IIIb) or (IIIc)

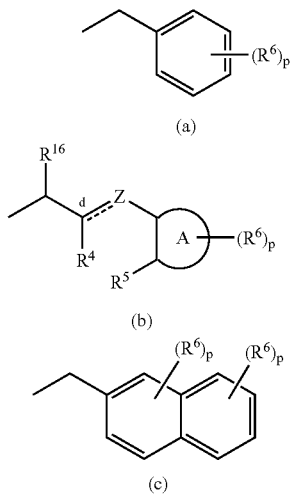

wherein:
- d is a single bond while Z is either a bivalent radical selected from the group of —CH₂—, —C(=O)—, —CH(OH)—, —C(=N—OH)—, —CH(alkyl)-, —O—, —S—, —S(=O)—, —NH— and —SH—; or Z is a trivalent CH-moiety that forms a covalent bond with R⁴ equal to alkyl, such that a cycloalkyl moiety is formed; or d is a double bond while Z is either a trivalent radical of formula =CH— or =C(alkyl)-; or Z is a trivalent CH-moiety that forms a covalent bond with R⁴ equal to alkyl, such that a cycloalkenyl moiety is formed;
- A is a 5- or 6-membered aromatic homocyclic or heterocyclic ring, selected from the group of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;
- p is an integer ranging from 0 to 6;
- R⁴ and R⁵ are each, independently from each other, selected from the group of hydrogen, alkyl, Ar, biphenyl, halo and cyano ; or
- R⁴ and R⁵ may be taken together to form a bivalent radical —R⁴—R⁵— selected from the group of —CH₂—, =CH—, —CH₂—CH₂—, —CH=CH—, —O—, —NH—, =N—, —S—, —CH₂N(-alkyl)-, —N(-alkyl)CH₂—, —CH₂NH—, —NHCH₂—, —CH=N—, —N=CH—, —CH₂O— and —OCH₂—;
- each R⁶ is independently from each other, selected from the group of hydroxy, amino, nitro, cyano, halo, carboxyl, alkyl, Ar, alkyloxy, Ar-oxy, alkylcarbonyloxy, alkyloxycarbonyl, alkylthio, mono- and di(alkyl)amino, alkylcarbonylamino, mono- and di(alkyl)aminocarbonyl, mono- and di(alkyl)aminocarbonyloxy, mono- and di(alkyl)aminoalkyloxy; or
- two vicinal radicals R may be taken together to form a bivalent radical —R⁶—R⁶— selected from the group of —CH₂—CH₂—O—, —O—CH₂—CH₂—, —O—CH₂—C(=O)—, —C(=O)—CH₂—O—, —O—CH₂—O—, —CH₂—O—CH₂—, —O—CH₂—CH₂—O—, —CH₂—O—, —CH=CH—CH=CH—, —CH=CH—CH=N—, —CH=CH—,N=CH—, —CH=N—CH=CH—, —N=CH—CH=CH—, —CH₂—CH₂—CH₂—, —CH₂—CH₂—C(=O)—, —C(=O)—CH₂—CH₂—, —CH₂—C(=O)—CH₂— and —CH₂—CH₂—CH₂—CH₂—; and
- R¹⁶ is selected from the group of hydrogen, alkyl, Ar and Ar-alkyl;
- alkyl represents a straight or branched saturated hydrocarbon radical having from 1 to 6 carbon atoms or a cyclic saturated hydrocarbon radical having from 3 to 6 carbon atoms, optionally substituted with one or more methyl, halo, cyano, oxo, hydroxy, alkyloxy or amino radicals;
- alkenyl represents a straight or branched unsaturated hydrocarbon radical having one or more double bonds, optionally substituted with one or more methyl, halo, cyano, oxo, hydroxy, alkyloxy or amino radicals;
- Ar represents phenyl or naphthyl, optionally substituted with one or more radicals selected from the group of alkyl, halo, cyano, hydroxy, alkyloxy and amino; and
- Het is a monocyclic heterocyclic radical selected from the group of azetidinyl, pyrrolidinyl, piperidinyl, homopiperidinyl, morpholinyl, piperazinyl, tetrahydrofuranyl, pyridinyl, and benzylpiperazinyl.

2. A compound according to claim 1, wherein
X is O;
R¹ and R² each selected from the group of hydrogen, N—R¹⁰R¹¹ and alkyloxy; with the proviso that at least one of R¹ and R² is N—R¹⁰R¹¹ wherein:
- R¹⁰ and R¹¹ are each, independently from each other, selected from the group of hydrogen, alkyl, Het, Ar, Ar-alkyl, Het-alkyl, mono- or di(alkyl)aminoalkyl, mono- or di(alkenyl)aminoalkyl, alkylcarbonyl, alkenylcarbonyl, Ar-carbonyl, Het-carbonyl, alkyloxycarbonyl, aminocarbonyl, mono- or di(alkyl)aminocarbonyl, mono- or di(Ar)aminocarbonyl, mono- or di(alkyloxycarbonylalkyl)aminocarbonyl, alkylcarbonyloxyalkyl, alkenylcarbonyloxyalkyl, mono- or di(alkyl)aminocarbonyloxyalkyl, N-benzylpiperazinyliminomethyl, alkylsulphonyl and Ar-sulphonyl; or
- R¹⁰ and R¹¹ may be taken together and with the N may form a monovalent radical selected from the group of

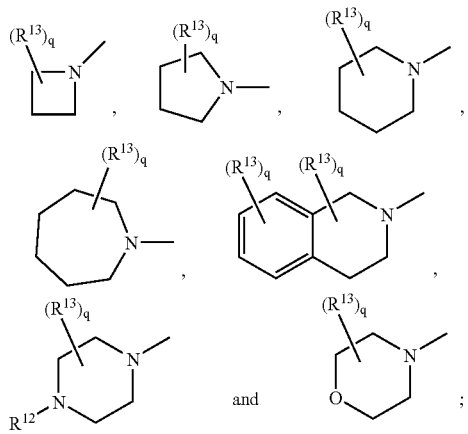

wherein:
R¹² selected from the group of hydrogen, alkyl, Ar, Ar-alkyl and Ar-alkenyl; each ring having optionally a double bond and each ring being optionally substituted with q radicals R¹³, each radical R¹³ independently from each other selected from the group of alkyl, oxo and alkyloxycarbonyl and q being an integer ranging from 0 to 2;

a and b are asymmetric centers;

$(CH_2)_m$ is a straight hydrocarbon chain of m carbon atoms, m being an integer equal to 1;

Pir is a radical according to Formula (IIa)

$R^3$ represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O, N and S;

alkyl represents a straight or branched saturated hydrocarbon radical having from 1 to 6 carbon atoms or a cyclic saturated hydrocarbon radical having from 3 to 6 carbon atoms, optionally substituted with one or more methyl or amino radicals;

alkenyl represents a straight or branched unsaturated hydrocarbon radical having one or more double bonds, optionally substituted with one or more methyl radicals;

Ar represents phenyl, optionally substituted with one or more radicals selected from the group of alkyl, halo, cyano, hydroxy and alkyloxy; and Het is a monocyclic heterocyclic radical selected from the group of azetidinyl, pyrrolidinyl, piperidinyl, homopiperidinyl, morpholinyl, piperazinyl, N-benzylpiperazinyl, tetrahydrofuranyl and pyridinyl.

3. A compound according claim 1, wherein $R^3$ is a radical according to any one of Formula (IIIa), (IIIb) or (IIIc) wherein:

d is a double bond while Z is a trivalent radical of formula =CH—, or =C(alkyl)-;

A is phenyl, p is an integer equal to 0 or 1;

$R^4$ and $R^5$ are each, independently from each other, selected from the group of hydrogen and alkyl;

each $R^6$ is halo; and $R^{16}$ is hydrogen.

4. A compound according to claim 1, wherein X=O, one of $R^1$ and $R^2$ is hydrogen, methoxy or ethoxy ; m=1; Pir is a radical according to Formula (IIa) wherein n=0; $R^3$ is a radical according to Formula (IIIb) wherein Z is =CH—, d is a double bond, A is a phenyl ring, $R^4$ is methyl and $R^5$ and $R^{16}$ are each hydrogen.

5. A compound according to claim 1, wherein $R^1$ is hydrogen or methoxy and $R^2$ is an amine radical $NR^{10}R^{11}$ ; X=O; m =1; Pir is a radical according to Formula (IIa) wherein n =0; $R^3$ is a radical according to Formula (IIIb) wherein Z is =CH—, d is a double bond, A is a phenyl ring, $R^4$ is methyl and $R^5$ and $R^{16}$ are each hydrogen.

6. A pharmaceutical composition comprising a pharmaceutically acceptable caffier and, as active ingredient, a therapeutically effective amount of a compound according to claim 1.

7. A process for making a pharmaceutical composition, comprising mixing a compound according to claim 1 and a pharmaceutically acceptable carrier.

8. A pharmaceutical composition comprising a pharmaceutically acceptable carrier and, as active ingredient, a therapeutically effective amount of a compound according to claim 1, and one or more other compounds selected from the group of antidepres sants, anxiolytics and antipsychotics.

9. A method for the treatment of depression, anxiety and eating disorders, said treatment comprising the simultaneous or sequential administration of a therapeutically effective amount of a compound according to claim 1, and one or more other compounds selected from the group of antidepressants, anxiolytics and antipsychotics, to a patient in need of treatment.

10. A process for making a pharmaceutical composition comprising mixing a compound according to claim 1, and a compound selected from the group of antidepressants, anxiolytics and antipsychotics and a pharmaceutically acceptable carrier.

11. A process for preparing a compound according to Formula (I),

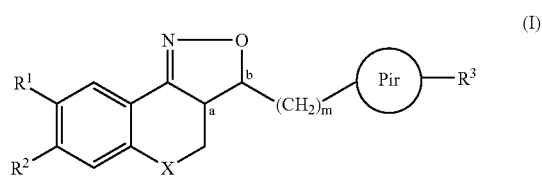

the pharmaceutically acceptable acid or base addition salts thereof, the stereochemically isomeric forms thereof and the N-oxide form thereof, wherein:

X is $CH_2$, $N—R^7$, S or O;

$R^7$ is selected from the group of hydrogen, alkyl, Ar, Ar-alkyl, alkylcarbonyl, alkyloxycarbonyl and mono- and di(alkyl)aminocarbonyl;

wherein at least one of $R^1$ and $R^2$ a halogen and at most one of $R^1$ and $R^2$ selected from the group of hydrogen, hydroxy, cyano, halo, $OSO_2H$, $OSO_2CH_3$, $N—R^{10}R^{11}$, alkyloxy, alkyloxyalkyloxy, alkyloxyalkyloxyalkyloxy, tetrahydrofuranyloxy, alkylthio, alkylcarbonyloxy, alkyloxyalkylcarbonyloxy, pyridinylcarbonyloxy, alkylcarbonyloxyalkyloxy, alkyloxycarbonyloxy, alkenyloxy, alkenyl-carbonyloxy and mono- or di(alkyl)aminoalkyloxy;

with the proviso that at least one of $R^1$ and $R^2$ is $N—R^{10}R^{11}$ wherein:

$R^{10}$ and $R^{11}$ are each, independently from each other, selected from the group of hydrogen, alkyl, Het, Ar, Ar-alkyl, Het- alkyl, mono- or di(alkyl)aminoalkyl, mono- or di(alkenyl)aminoalkyl, alkylcarbonyl, alkenylcarbonyl, Ar-carbonyl, Het-carbonyl, alkyloxycarbonyl, aminocarbonyl, mono- or di(alkyl)aminocarbonyl, mono- or di(Ar)aminocarbonyl, mono- or di(alkyloxycarbonylalkyl)aminocarbonyl, alkylcarbonyloxyalkyl, alkenylcarbonyloxyalkyl, mono- or di(alkyl)aminocarbonyloxyalkyl, aminoiminomethyl, alkylaminoiminomethyl, N-benzylpiperazinyliminomethyl, alkylsulphonyl and Ar-sulphonyl ; or $R^{10}R^{11}$ may be taken together and with the N may form a monovalent radical selected from the group of

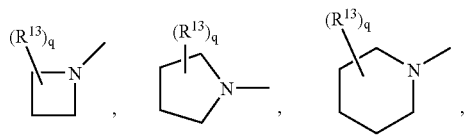

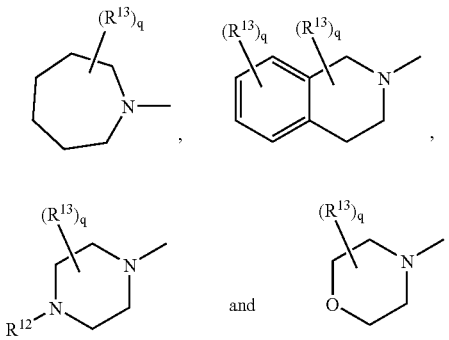

wherein:
R$^{12}$ selected from the group of hydrogen, alkyl, Ar, Ar-alkyl, Ar-alkenyl, alkylcarbonyl, alkyloxycarbonyl, alkyloxyalkylcarbonyl and mono- or di(alkyl)-aminocarbonyl;

each ring having optionally 1, 2 or 3 double bonds and each ring being optionally substituted with q radicals R$^{13}$, each radical R$^{13}$ independently from each other selected from the group of alkyl, oxo, Ar, Ar-alkyl, Ar-alkenyl and alkyloxycarbonyl and q being an integer ranging from 0 to 6;

a and b are asymmetric centers;

(CH$_2$)$_m$ is a straight hydrocarbon chain of m carbon atoms, m being an integer ranging from 1 to 4;

Pir is a radical according to any one of Formula (IIa), (IIb) or (IIc)

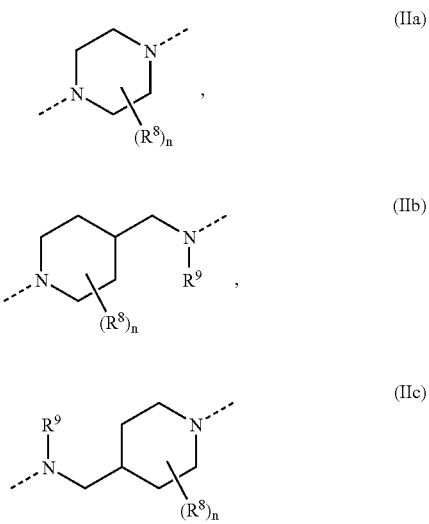

optionally substituted with n radicals R$^8$, wherein:
each R$^8$ is independently from each other, selected from the group of hydroxy, amino, nitro, cyano, halo and alkyl;
n is an integer ranging from 0 to 5;
R$^9$ is selected from the group of hydrogen, alkyl and formyl;

R$^3$ is a radical according to any one of Formula (IIIa), (IIIb) or (IIIc)

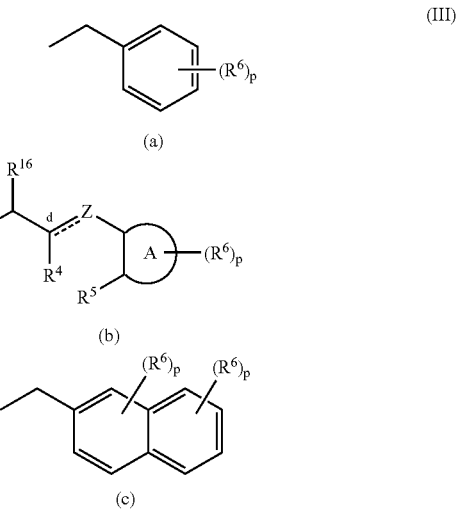

wherein:
d is a single bond while Z is either a bivalent radical selected from the group of —CH$_2$—, —C(=O)—, —CH(OH)—, —C(=N—OH)—, —CH(alkyl)—, —O—, —S—, —S(=O)—, —NH— and —SH—; or Z is a trivalent CH-moiety that forms a covalent bond with R$^4$ equal to alkyl, such that a cycloalkyl moiety is formed; or d is a double bond while Z is either a trivalent radical of formula =CH—, or =C(alkyl)—; or Z is a trivalent CH-moiety that forms a covalent bond with R$^4$ equal to alkyl, such that a cycloalkenyl moiety is formed;

A is a 5- or 6-membered aromatic homocyclic or heterocyclic ring, selected from the group of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;

p is an integer ranging from 0 to 6;

R$^4$ and R$^5$ are each, independently from each other, selected from the group of hydrogen, alkyl, Ar, biphenyl, halo and cyano; or R$^4$ and R$^5$ may be taken together to form a bivalent radical —R$^4$—R$^5$— selected from the group of —CH$_2$—, =CH—, —CH$_2$—CH$_2$—, —CH=CH—, —O—, —NH—, =N—, —S—, —CH$_2$N(-alkyl)-, —N(-alkyl)CH$_2$—, —CH$_2$NH—, —NHCH$_2$—, —CH=N—, —N=CH—, —CH$_2$O— and —OCH$_2$—;

each R$^6$ is independently from each other, selected from the group of hydroxy, amino, nitro, cyano, halo, carboxyl, alkyl, Ar, alkyloxy, Ar-oxy, alkylcarbonyloxy, alkyloxycarbonyl, alkylthio, mono- and di(alkyl)amino, alkylcarbonylamino, mono- and di(alkyl)aminocarbonyl, mono- and di(alkyl)aminocarbonyloxy, mono- and di(alkyl)aminoalkyloxy; or two vicinal radicals R$^6$ may be taken together to form a bivalent radical —R$^6$—R$^6$— selected from the group of —CH$_2$—CH$_2$—O—, —O—CH$_2$—CH$_2$—, —O—CH$_2$—C(=O)—, —C(=O)—CH$_2$—O—, —O—CH$_2$—O—, —CH$_2$—O—CH$_2$—, —O—CH$_2$—CH$_2$—O—, —CH=CH—CH=CH—, —CH=CH—CH=N—, —CH=CH—N=CH—, —CH=N—

—CH=CH—, —N=CH—CH=CH—, —CH$_2$—CH$_2$—CH$_2$—, —CH$_2$—CH$_2$—C(=O)—, —C(=O)—CH$_2$—CH$_2$—, —CH$_2$—C(=O)—CH$_2$— and —CH$_2$—CH$_2$—CH$_2$—CH$_2$—; and R$^{16}$ is selected from the group of hydrogen, alkyl, Ar and Ar-alkyl;

alkyl represents a straight or branched saturated hydrocarbon radical having from 1 to 6 carbon atoms or a cyclic saturated hydrocarbon radical having from 3 to 6 carbon atoms, optionally substituted with one or more methyl, halo, cyano, oxo, hydroxy, alkyloxy or amino radicals;

alkenyl represents a straight or branched unsaturated hydrocarbon radical having one or more double bonds, optionally substituted with one or more methyl, halo, cyano, oxo, hydroxy, alkyloxy or amino radicals;

Ar represents phenyl or naplithyl, optionally substituted with one or more radicals selected from the group of alkyl, halo, cyano, hydroxy, alkyloxy and amino; and Het is a monocyclic heterocyclic radical selected from the group of azetidinyl, pyrrolidinyl, piperidinyl, homopiperidinyl, morpholinyl, piperazinyl, tetrahydrofuranyl, pyridinyl, and benzvlpiperazinvl;

wherein a compound according to Formula (IV) is reacted with an amine of Formula (V) according to the following reaction

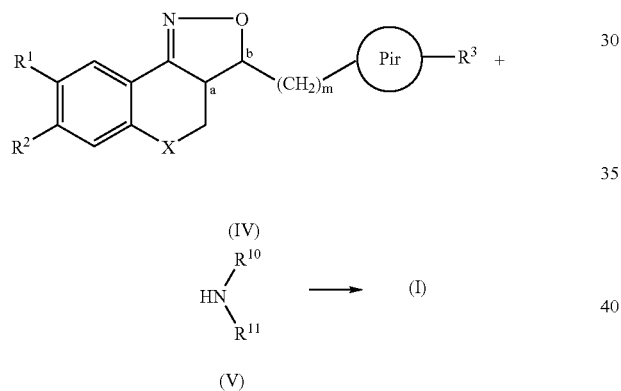

12. A compound according to the general Formula (I)

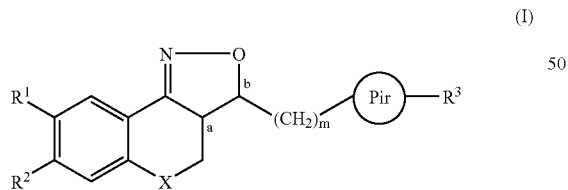

the pharmaceutically acceptable acid or base addition salts thereof, the stereochemically isomeric forms thereof and the N-oxide form thereof, wherein:

X is O;

R$^7$ is selected from the group of hydrogen, alkyl, Ar, Ar-alkyl, alkylcarbonyl, alkyloxycarbonyl and mono- and di(alkyl)aminocarbonyl;

R$^1$ and R$^2$ are each selected from the group of hydrogen, hydroxy, cyano, halo, OSO$_2$H, OSO$_2$CH$_3$, N—R$^{10}$R$^{11}$, alkyloxy, alkyloxyalkyloxy, alkyloxyalkyloxyalkyloxy, tetrahydrofuranyloxy, alkylthio, alkylcarbonyloxy, alkyloxyalkylcarbonyloxy, pyridinylcarbonyloxy, alkylcarbonyloxyalkyloxy, alkyloxycarbonyloxy, alkenyloxy, alkenylcarbonyloxy and mono- or di(alkyl)aminoalkyloxy;

with the proviso that at least one of R$^1$ and R$^2$ is N—R$^{10}$R$^{11}$ wherein:

R$^{10}$ and R$^{11}$ are each, independently from each other, selected from the group of hydrogen, alkyl, Het, Ar, Ar-alkyl, Het-alkyl, mono- or di(alkyl)aminoalkyl, mono- or di(alkenyl)aminoalkyl, alkylcarbonyl, alkenylcarbonyl, Ar-carbonyl, Het-carbonyl, alkyloxycarbonyl, aminocarbonyl, mono- or di(alkyl)aminocarbonyl, mono- or di(Ar)aminocarbonyl, mono- or di(alkyloxycarbonylalkyl)aminocarbonyl, alkylcarbonyloxyalkyl, alkenylcarbonyloxyalkyl, mono- or di(alkyl)aminocarbonyloxyalkyl, aminoiminomethyl, alkylaminoiminomethyl, N-benzylpiperazinyliminomethyl, alkylsulphonyl and Ar-sulphonyl; or R$^{10}$R$^{11}$ may be taken together and with the N may form a monovalent radical selected from the group of

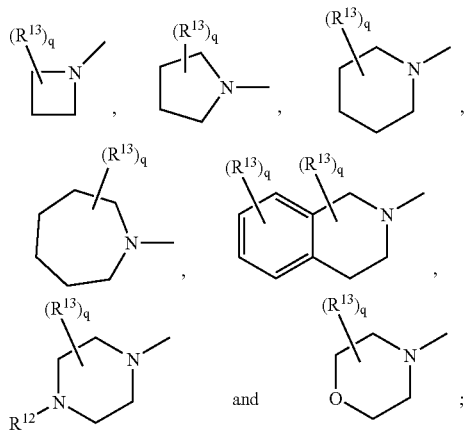

wherein:

R$^{12}$ is selected from the group of hydrogen, alkyl, Ar, Ar-alkyl, Ar-alkenyl, alkylcarbonyl, alkyloxycarbonyl, alkyloxyalkylcarbonyl and mono- or di(alkyl)-aminocarbonyl;

each ring having optionally 1, 2 or 3 double bonds and each ring being optionally substituted with q radicals R$^{13}$, each radical R$^{13}$ independently from each other selected from the group of alkyl, oxo, Ar, Ar-alkyl, Ar-alkenyl and alkyloxycarbonyl and q being an integer ranging from 0 to 6 ; or R$^1$ and R$^2$ may be taken together to form a bivalent radical —R$^1$—R$^2$—selected from the group of —O—CH$_2$—NR$^{14}$—, —NR$^{14}$—CH$_2$—O—, —NR$^{15}$—CH$_2$—NR$^{14}$—, —NR$^{14}$—CH$_2$CH$_2$—O—, —O—CH$_2$—CH$_2$—NR$^{14}$—, —NR$^{15}$—CH$_2$—CH$_2$—NR$^{14}$—, —wherein R$^{14}$ and R$^{15}$ each, independently from each other, are selected from the group of hydrogen, alkyl, Ar, Ar-alkyl, alkylcarbonyl, alkyloxycarbonyl, alkyloxyalkylcarbonyl and mono- or di(alkyl)aminocarbonyl;

a and b are asymmetric centers;

(CH$_2$)$_m$ is a straight hydrocarbon chain of m carbon atoms, m being an integer ranging from 1 to 4;

Pir is a radical according to any one of Formula (IIa), (IIb) or (IIc)

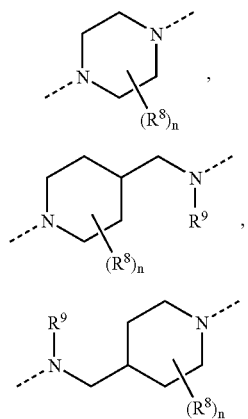

optionally substituted with n radicals $R^8$, wherein each $R^8$ is independently from each other, selected from the group of hydroxy, amino, nitro, cyano, halo and alkyl;

n is an integer ranging from 0 to 5;

$R^9$ is selected from the group of hydrogen, alkyl and formyl;

$R^3$ is a radical according to any one of Formula (IIIa), (IIIb) or (IIIc)

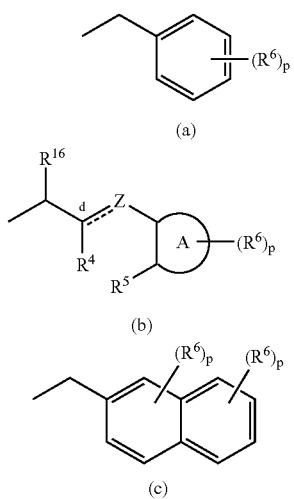

wherein:
d is a single bond while Z is either a bivalent radical selected from the group of —$CH_2$—, —C(=O)—, —CH(OH)—, —C(=N—OH)—, —CH(alkyl)—, —O—, —S—, —S(=O)—, —NH— and —SH—; or Z is a trivalent CH-moiety that forms a covalent bond with $R^4$ equal to alkyl, such that a cycloalkyl moiety is formed; or d is a double bond while Z is either a trivalent radical of formula =CH—, or =C(alkyl)—; or Z is a trivalent CH-moiety that forms a covalent bond with $R^4$ equal to alkyl, such that a cycloalkenyl moiety is formed;

A is a 5- or 6-membered aromatic homocyclic or heterocyclic ring, selected from the group of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;

p is an integer ranging from 0 to 6;

$R^4$ and $R^5$ are each, independently from each other, selected from the group of hydrogen, alkyl, Ar, biphenyl, halo and cyano; or $R^4$ and $R^5$ may be taken together to form a bivalent radical —$R^4$—$R^5$- selected from the group of —$CH_2$—, =CH—, —$CH_2$—$CH_2$—, —CH=CH—, —O—, —NH—, =N—, —S—, —$CH_2$N(-alkyl)—, —N(-alkyl)$CH_2$—, —$CH_2$NH—, —NH$CH_2$—, —CH=N—, —N=CH—, —$CH_2$O— and —O$CH_2$—;

each $R^6$ is independently from each other, selected from the group of hydroxy, amino, nitro, cyano, halo, carboxyl, alkyl, Ar, alkyloxy, Ar-oxy, alkylcarbonyloxy, alkyloxycarbonyl, alkylthio, mono- and di(alkyl)amino, alkylcarbonylamino, mono- and di(alkyl)aminocarbonyl, mono- and di(alkyl)aminocarbonyloxy, mono- and di(alkyl)aminoalkyloxy; or two vicinal radicals $R^6$ may be taken together to form a bivalent radical —$R^6$—$R^6$- selected from the group of —$CH_2$—$CH_2$—O—, —O—$CH_2$—$CH_2$—, —O—$CH_2$—C(=O)—, —C(=O)—$CH_2$—O—, —O—$CH_2$—O—, —$CH_2$—O—$CH_2$—, —O—$CH_2$—$CH_2$—O—, —CH=CH—CH=CH—, —CH=CH—CH=N—, —CH=CH—N=CH—, —CH=N—CH=CH—, —N=CH—CH=CH—, —$CH_2$—$CH_2$—$CH_2$—, —$CH_2$—$CH_2$—C(=O)—, —C(=O)—$CH_2$—$CH_2$—, —$CH_2$—C(=O)—$CH_2$— and —$CH_2$—$CH_2$—$CH_2$—$CH_2$—; and $R^{16}$ is selected from the group of hydrogen, alkyl, Ar and Ar-alkyl;

alkyl represents a straight or branched saturated hydrocarbon radical having from 1 to 6 carbon atoms or a cyclic saturated hydrocarbon radical having from 3 to 6 carbon atoms, optionally substituted with one or more methyl, halo, cyano, oxo, hydroxy, alkyloxy or amino radicals;

alkenyl represents a straight or branched unsaturated hydrocarbon radical having one or more double bonds, optionally substituted with one or more methyl, halo, cyano, oxo, hydroxy, alkyloxy or amino radicals;

Ar represents phenyl or naphthyl, optionally substituted with one or more radicals selected from the group of alkyl, halo, cyano, hydroxy, alkyloxy and amino; and Het is a monocyclic heterocyclic radical selected from the group of azetidinyl, pyrrolidinyl, piperidinyl, homopiperidinyl, morpholinyl, piperazinyl, tetrahydrofuranyl, pyridinyl, and benzylpiperazinyl.

* * * * *

UNITED STATES PATENT AND TRADEMARK OFFICE
CERTIFICATE OF CORRECTION

PATENT NO. : 7,265,103 B2  
APPLICATION NO. : 10/510220  
DATED : September 4, 2007  
INVENTOR(S) : José Ignacio Andrés-Gil et al.

It is certified that error appears in the above-identified patent and that said Letters Patent is hereby corrected as shown below:

<u>Title Page</u>,  
Item (30) Foreign Application Priority Data:  
After "02076239" insert -- .9 --.

<u>Column 3</u>,  
Lines 27-34, delete

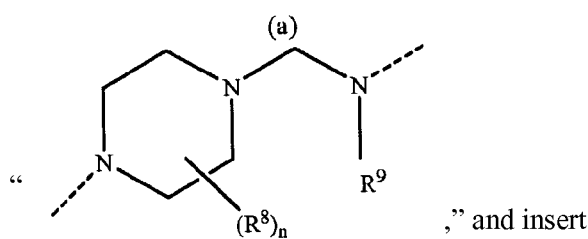

," and insert

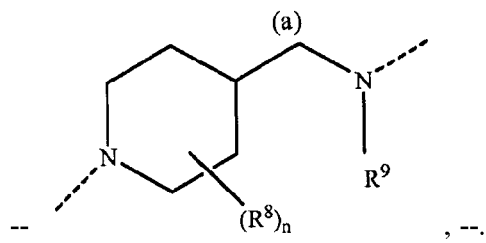

, --.

<u>Column 9</u>,  
Line 48, delete "(" before "$\alpha_2$-adrenoceptor".

<u>Column 15</u>,  
Line 39, delete "suitabele" and insert -- suitable --.

<u>Column 19</u>,  
Line 48, delete "," after "60° C.".

UNITED STATES PATENT AND TRADEMARK OFFICE
CERTIFICATE OF CORRECTION

PATENT NO. : 7,265,103 B2
APPLICATION NO. : 10/510220
DATED : September 4, 2007
INVENTOR(S) : José Ignacio Andrés-Gil et al.

It is certified that error appears in the above-identified patent and that said Letters Patent is hereby corrected as shown below:

Column 30,
Lines 4-12, delete

"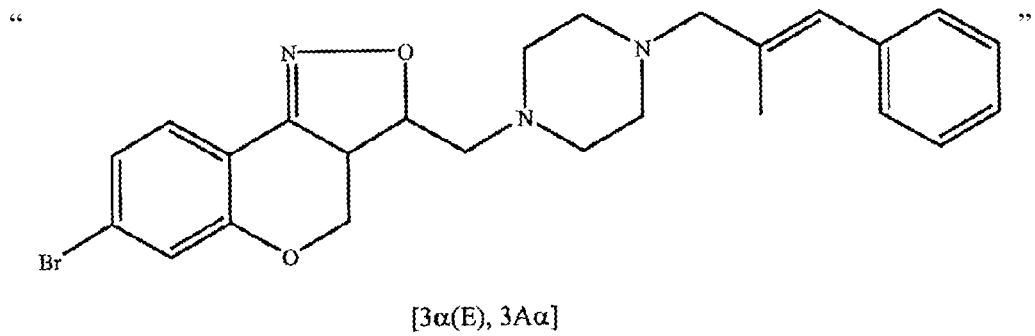"

[3α(E), 3Aα]

and insert

--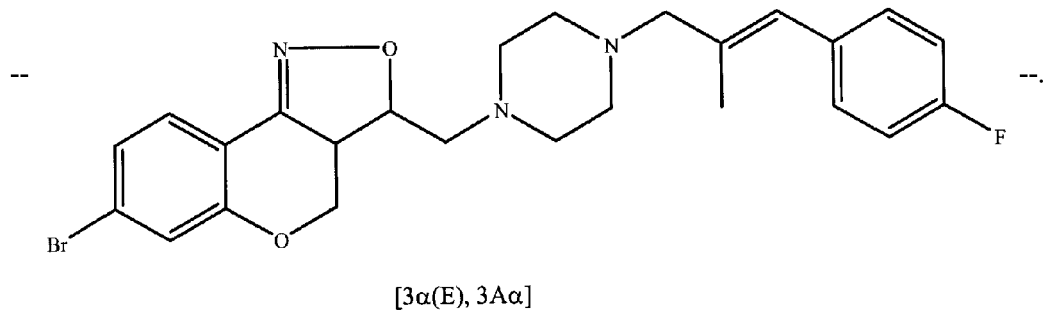--.

[3α(E), 3Aα]

UNITED STATES PATENT AND TRADEMARK OFFICE
CERTIFICATE OF CORRECTION

PATENT NO. : 7,265,103 B2
APPLICATION NO. : 10/510220
DATED : September 4, 2007
INVENTOR(S) : José Ignacio Andrés-Gil et al.

It is certified that error appears in the above-identified patent and that said Letters Patent is hereby corrected as shown below:

Column 31,
Lines 8-16, delete

" 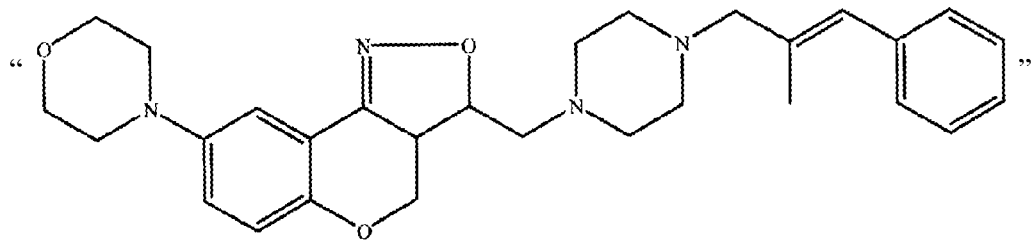 "

[3α(E), 3Aα]

and insert

-- 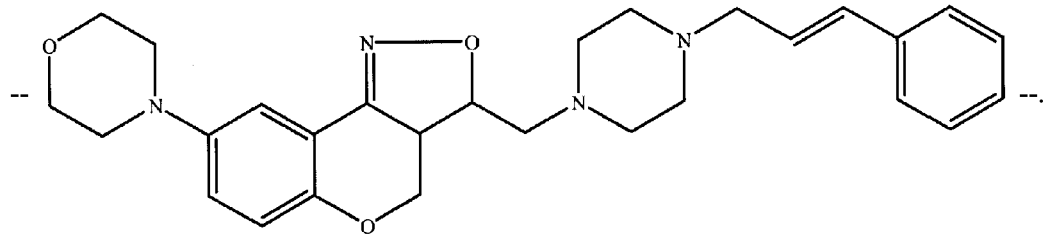 --.

[3α(E), 3Aα]

UNITED STATES PATENT AND TRADEMARK OFFICE
CERTIFICATE OF CORRECTION

PATENT NO. : 7,265,103 B2  
APPLICATION NO. : 10/510220  
DATED : September 4, 2007  
INVENTOR(S) : José Ignacio Andrés-Gil et al.

Page 4 of 5

It is certified that error appears in the above-identified patent and that said Letters Patent is hereby corrected as shown below:

Column 32,
Lines 25-35, delete

"
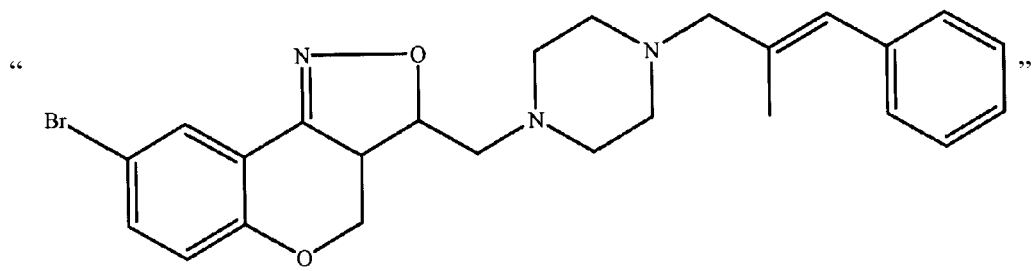
"

[3α(E), 3Aα]

and insert

--
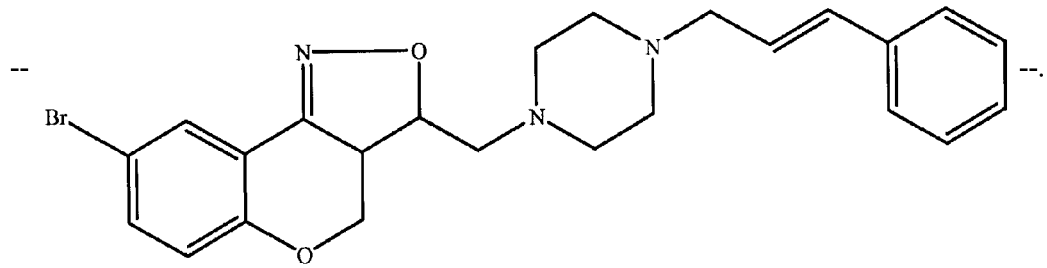
--.

[3α(E), 3Aα]

Column 66,
Line 48, delete "Filtermatel 96" and insert -- Filtermate 196 --.
Lines 67-Col. 67, line 1, delete "Filtermatel 96" and insert -- Filtermate 196 --.

Column 71,
Line 61, delete "R" and insert -- $R^6$ --.
Line 64, delete "–C (=O)–CH$_2$–O–," and insert -- –C(=O)–CH$_2$–O–, --.

Column 73,
Line 67, delete "eating" and insert -- body weight --.

UNITED STATES PATENT AND TRADEMARK OFFICE
CERTIFICATE OF CORRECTION

PATENT NO. : 7,265,103 B2
APPLICATION NO. : 10/510220
DATED : September 4, 2007
INVENTOR(S) : José Ignacio Andrés-Gil et al.

It is certified that error appears in the above-identified patent and that said Letters Patent is hereby corrected as shown below:

Column 74,
Line 32, after "$R^1$ and $R^2$" insert -- is --.
Line 57, delete "$R^{10}R^{11}$" and insert -- $R^{10}$ and $R^{11}$ --.

Column 75,
Line 19, after "$R^{12}$" insert -- is --.

Column 77,
Line 17, delete "naplithyl," and insert -- naphthyl, --.
Line 23, delete "benzvlpiperazinvl;" and insert -- benzylpiperazinyl; --.

Column 80,
Line 2, after "=CH–" delete ",".

Signed and Sealed this

Twenty-eighth Day of October, 2008

JON W. DUDAS
*Director of the United States Patent and Trademark Office*